(12) United States Patent
Clawson

(10) Patent No.: US 8,066,638 B2
(45) Date of Patent: Nov. 29, 2011

(54) DIAGNOSTIC AND INTERVENTION TOOLS FOR EMERGENCY MEDICAL DISPATCH

(76) Inventor: Jeffrey J. Clawson, Salt Lake City, UT (US)

(*) Notice: Subject to any disclaimer, the term of this patent is extended or adjusted under 35 U.S.C. 154(b) by 250 days.

(21) Appl. No.: 12/396,201

(22) Filed: Mar. 2, 2009

(65) Prior Publication Data

US 2009/0168975 A1    Jul. 2, 2009

Related U.S. Application Data

(63) Continuation of application No. 11/818,181, filed on Jun. 13, 2007, now Pat. No. 7,645,234.

(51) Int. Cl.
*A61B 5/00* (2006.01)
(52) U.S. Cl. .................. 600/300; 705/2; 128/920
(58) Field of Classification Search .................. 600/300, 600/301; 128/903–905, 920
See application file for complete search history.

(56) References Cited

U.S. PATENT DOCUMENTS

| | | | |
|---|---|---|---|
| 3,799,147 A | 3/1974 | Adolph et al. |
| 4,130,881 A | 12/1978 | Haessler et al. |
| 4,164,320 A | 8/1979 | Irazoqui et al. |
| 4,237,344 A | 12/1980 | Moore |
| 4,290,114 A | 9/1981 | Sinay |
| 4,338,493 A | 7/1982 | Stenhuis et al. |
| 4,360,345 A | 11/1982 | Hon |
| 4,455,548 A | 6/1984 | Burnett |
| 4,489,387 A | 12/1984 | Lamb et al. |
| 4,731,725 A | 3/1988 | Suto et al. |
| 4,839,822 A | 6/1989 | Dormond et al. |
| 4,858,121 A | 8/1989 | Barber et al. |
| 4,865,549 A | 9/1989 | Sonsteby |
| 4,922,514 A | 5/1990 | Bergeron et al. |
| 4,926,495 A | 5/1990 | Comroe et al. |
| 4,945,476 A | 7/1990 | Bodick et al. |
| 4,967,754 A | 11/1990 | Rossi |
| 5,063,522 A | 11/1991 | Winters |
| 5,065,315 A | 11/1991 | Garcia |
| 5,072,383 A | 12/1991 | Brimm et al. |
| 5,077,666 A | 12/1991 | Brimm et al. |
| 5,086,391 A | 2/1992 | Chambers |
| 5,109,399 A | 4/1992 | Thompson |
| 5,122,959 A | 6/1992 | Nathanson et al. |

(Continued)

FOREIGN PATENT DOCUMENTS

JP    2003-187003 A    7/2003

(Continued)

OTHER PUBLICATIONS

Notification of Transmittal of the International Search Report (2 pgs.), International Search Report, (2 pgs.), and Written Opinion (8 pgs.) mailed from International Searching Authority on Jun. 10, 2009.

(Continued)

*Primary Examiner* — Henry M Johnson, III
*Assistant Examiner* — Kai Rajan
(74) *Attorney, Agent, or Firm* — John R. Thompson; Stoel Rives LLP

(57) ABSTRACT

A system and method assists an emergency medical dispatcher in responding to emergency calls. A computer implemented emergency medical dispatch protocol includes interrogatories for a dispatcher to ask a caller to generate an appropriate response. A diagnostic tool is provided to determine a vital sign of a patient based on a timer and caller relayed information about the patient. An intervention tool is provided to administer assistance and determine a compression rate based on a timer and caller relayed information.

62 Claims, 19 Drawing Sheets

U.S. PATENT DOCUMENTS

| | | |
|---|---|---|
| 5,193,855 A | 3/1993 | Shamos |
| 5,228,449 A | 7/1993 | Christ et al. |
| 5,253,164 A | 10/1993 | Holloway et al. |
| 5,255,187 A | 10/1993 | Sorensen |
| 5,291,399 A | 3/1994 | Chaco |
| 5,323,444 A | 6/1994 | Ertz et al. |
| 5,339,351 A | 8/1994 | Hoskinson et al. |
| 5,348,008 A | 9/1994 | Bornn et al. |
| 5,379,337 A | 1/1995 | Castillo et al. |
| 5,404,292 A | 4/1995 | Hendrickson |
| 5,410,471 A | 4/1995 | Alyfuku et al. |
| 5,423,061 A | 6/1995 | Fumarolo et al. |
| 5,438,996 A | 8/1995 | Kemper et al. |
| 5,441,047 A | 8/1995 | David et al. |
| 5,462,051 A | 10/1995 | Oka et al. |
| 5,471,382 A | 11/1995 | Tallman et al. |
| 5,502,726 A | 3/1996 | Fischer |
| 5,513,993 A | 5/1996 | Lindley et al. |
| 5,516,702 A | 5/1996 | Senyei et al. |
| 5,521,812 A | 5/1996 | Feder et al. |
| 5,536,084 A | 7/1996 | Curtis et al. |
| 5,544,649 A | 8/1996 | David et al. |
| 5,554,031 A | 9/1996 | Moir et al. |
| 5,590,269 A | 12/1996 | Kruse et al. |
| 5,594,638 A | 1/1997 | Iliff |
| 5,594,786 A | 1/1997 | Chaco et al. |
| 5,596,994 A | 1/1997 | Bro |
| 5,630,125 A | 5/1997 | Zellweger |
| 5,636,873 A | 6/1997 | Sonsteby |
| 5,650,995 A | 7/1997 | Kent |
| 5,660,176 A | 8/1997 | Iliff |
| 5,675,372 A | 10/1997 | Aguayo, Jr. et al. |
| 5,682,419 A | 10/1997 | Grube et al. |
| 5,684,860 A | 11/1997 | Milani et al. |
| 5,689,229 A | 11/1997 | Chaco et al. |
| 5,719,918 A | 2/1998 | Serbetciouglu et al. |
| 5,722,418 A | 3/1998 | Bro |
| 5,724,983 A | 3/1998 | Selker et al. |
| 5,734,706 A | 3/1998 | Windsor et al. |
| 5,745,532 A | 4/1998 | Campana, Jr. |
| 5,748,907 A | 5/1998 | Crane |
| 5,754,960 A | 5/1998 | Downs et al. |
| 5,759,044 A | 6/1998 | Redmond |
| 5,761,278 A | 6/1998 | Pickett et al. |
| 5,761,493 A | 6/1998 | Blakeley et al. |
| 5,787,429 A | 7/1998 | Nikolin, Jr. |
| 5,805,670 A | 9/1998 | Pons et al. |
| 5,809,493 A | 9/1998 | Ahamed et al. |
| 5,822,544 A | 10/1998 | Chaco et al. |
| 5,823,948 A | 10/1998 | Ross, Jr. et al. |
| 5,826,077 A | 10/1998 | Blakeley et al. |
| 5,832,187 A | 11/1998 | Pedersen et al. |
| 5,842,173 A | 11/1998 | Strum et al. |
| 5,844,817 A | 12/1998 | Lobley et al. |
| 5,857,966 A | 1/1999 | Clawson |
| 5,901,214 A | 5/1999 | Shaffer et al. |
| 5,902,234 A | 5/1999 | Webb |
| 5,910,987 A | 6/1999 | Ginter et al. |
| 5,912,818 A | 6/1999 | McGrady et al. |
| 5,915,019 A | 6/1999 | Ginter et al. |
| 5,926,526 A | 7/1999 | Rapaport et al. |
| 5,933,780 A | 8/1999 | Connor et al. |
| 5,961,446 A | 10/1999 | Beller et al. |
| 5,962,891 A | 10/1999 | Arai |
| 5,964,700 A | 10/1999 | Tallman et al. |
| 5,986,543 A | 11/1999 | Johnson |
| 5,989,187 A | 11/1999 | Clawson |
| 5,991,730 A | 11/1999 | Lubin et al. |
| 5,991,751 A | 11/1999 | Rivette et al. |
| 6,004,266 A | 12/1999 | Clawson |
| 6,010,451 A | 1/2000 | Clawson |
| 6,022,315 A | 2/2000 | Iliff |
| 6,035,187 A | 3/2000 | Franza |
| 6,040,770 A | 3/2000 | Britton |
| 6,052,574 A | 4/2000 | Smith, Jr. |
| 6,053,864 A | 4/2000 | Clawson |
| 6,058,179 A | 5/2000 | Shaffer et al. |
| 6,074,345 A | 6/2000 | van Oostrom et al. |
| 6,076,065 A | 6/2000 | Clawson |
| 6,078,894 A | 6/2000 | Clawson et al. |
| 6,106,459 A | 8/2000 | Clawson |
| 6,112,083 A | 8/2000 | Sweet et al. |
| 6,115,646 A | 9/2000 | Fiszman et al. |
| 6,117,073 A | 9/2000 | Jones et al. |
| 6,118,866 A | 9/2000 | Shtivelman |
| 6,127,975 A | 10/2000 | Maloney |
| 6,134,105 A | 10/2000 | Lueker |
| 6,292,542 B1 | 9/2001 | Bilder |
| 6,370,234 B1 | 4/2002 | Kroll |
| 6,535,121 B2 | 3/2003 | Matheny |
| 6,607,481 B1 | 8/2003 | Clawson |
| 6,879,819 B2 | 4/2005 | Brooks |
| 6,901,397 B1 | 5/2005 | Moldenhauer et al. |
| 6,931,112 B1 | 8/2005 | McFarland et al. |
| 6,968,375 B1 | 11/2005 | Brown |
| 7,106,835 B2 | 9/2006 | Saalsaa |
| 7,428,301 B1 | 9/2008 | Clawson |
| 7,436,937 B2 | 10/2008 | Clawson |
| 2002/0004729 A1 | 1/2002 | Zak et al. |
| 2002/0106059 A1 | 8/2002 | Kroll et al. |
| 2003/0028536 A1 | 2/2003 | Singh et al. |
| 2003/0050538 A1 | 3/2003 | Naghavi et al. |
| 2003/0195394 A1 | 10/2003 | Saalsaa |
| 2003/0212575 A1 | 11/2003 | Saalsaa et al. |
| 2006/0122520 A1 | 6/2006 | Banet et al. |
| 2006/0173500 A1 | 8/2006 | Walker et al. |
| 2006/0178908 A1 | 8/2006 | Rappaport |
| 2007/0055559 A1 | 3/2007 | Clawson |
| 2007/0112275 A1 | 5/2007 | Cooke et al. |
| 2007/0116189 A1 | 5/2007 | Clawson |
| 2007/0201664 A1 | 8/2007 | Salafia et al. |
| 2010/0004710 A1 | 1/2010 | Kellum |
| 2010/0152800 A1 | 6/2010 | Walker et al. |

FOREIGN PATENT DOCUMENTS

| | | |
|---|---|---|
| WO | WO2006/015229 A2 | 2/2006 |
| WO | WO2008/156876 A1 | 12/2008 |

OTHER PUBLICATIONS

International Search Report and Written Opinion mailed Jan. 19, 2011 in PCT Application No. PCT/US2010/043308, filed Jul. 27, 2010.

International Search Report and Written Opinion mailed Jan. 19, 2011 in PCT Application No. PCT/US2010/043311, filed Jul. 27, 2010.

Radosevich, Lynda, "Network holds sway on life, death," Computerworld, v27 n21, May 24, 1993, 2 pgs.

Harris, Roger, "Updated 911 Phone System Top Concern of Residents," Business First-Louisville, v9 n19 s1, Dec. 1992, 3 pgs.

"Geac Completes Software Install," Wireless Week, Nov. 18, 1996, 3 pgs.

"Dictaphone introduces Windows-based Computer-Aided Dispatch (CAD) system," Business Wire, Apr. 23, 1996, 2 pgs. (in commercial use in 1995).

Holroyd, Brian, et al., "Medical Control; Quality Assurance in Prehospital Care," JAMA, the Journal of American Medical Association, v256, n8, Aug. 1986, p. 1027-1031.

CBS web page News Story entitled "911 Operator: 'It's got to be Hell'", Mar. 31, 2006 (excerpts from 911 operators' actions during the attacks on Sep. 11, 2001), 3 pgs.

Best, Wendy, "999 United Emergency services share life-saving Role to boost response," Western Daily Press, WDP Severnside ed., May 27, 1999, 2 pgs.

Poellmitz, William C., "Wireless technology keeps public safety a step ahead," Nation's Cities Weekly, v21 n17, Apr. 27, 1998, 3 pgs.

Crowley, Mark, "Learning from CAD System Implementation," Communications, v29 n8, Aug. 1992, 5 pgs.

Anonymous, "Suburban Chicago towns centralize 911 services," Communications News, v31 n10, Oct. 1994, 2 pgs.

Office Action Summary from USPTO for U.S. Appl. No. 10/255,901 mailed Dec. 31, 2003, 8 pgs.

Office Action Summary from USPTO for U.S. Appl. No. 10/255,901 mailed Oct. 13, 2004, 8 pgs.

Office Action Summary from USPTO for U.S. Appl. No. 10/255,901 mailed Jun. 29, 2005, 7 pgs.
Advisory Action Before the Filing of an Appeal Brief from USPTO for U.S. Appl. No. 10/255,901 mailed Feb. 14, 2006, 3 pgs.
Office Action Summary from USPTO for U.S. Appl. No. 10/255,901 mailed Jun. 7, 2006, 8 pgs.
Office Action Summary from USPTO for U.S. Appl. No. 10/255,901 mailed Feb. 27, 2007, 8 pgs.
Office Action Summary from USPTO for U.S. Appl. No. 10/255,901 mailed Sep. 6, 2007, 9 pgs.
Office Action Summary from USPTO for U.S. Appl. No. 10/255,905 mailed May 19, 2004, 7 pgs.
Office Action Summary from USPTO for U.S. Appl. No. 10/255,905 mailed May 26, 2005, 5 pgs.
Office Action Summary from USPTO for U.S. Appl. No. 10/255,905 mailed Feb. 9, 2006, 8 pgs.
Advisory Action Before the Filing of an Appeal Brief from USPTO for U.S. Appl. No. 10/255,905 mailed Aug. 11, 2006, 3 pgs.
Office Action Summary from USPTO for U.S. Appl. No. 10/255,905 mailed Jan. 30, 2007, 7 pgs.
Notice of Non-Compliant Amendment (37 CFR 1.121) from USPTO for U.S. Appl. No. 10/255,905 mailed Jul. 9, 2007, 4 pgs.
Office Action Summary from USPTO for U.S. Appl. No. 10/255,905 mailed Oct. 5, 2007, 7 pgs.
Office Action Summary from USPTO for U.S. Appl. No. 09/685,697 mailed Jul. 18, 2003, 8 pgs.
Office Action Summary from USPTO for U.S. Appl. No. 09/685,697 mailed Feb. 3, 2004, 5 pgs.
Office Action Summary from USPTO for U.S. Appl. No. 09/685,697 mailed Jan. 4, 2005, 5 pgs.
Office Action Summary from USPTO for U.S. Appl. No. 09/685,697 mailed Oct. 4, 2005, 7 pgs.
Advisory Action Before the Filing of an Appeal Brief from USPTO for U.S. Appl. No. 09/685,697 mailed Mar. 13, 2006, 4 pgs.
Office Action Summary from USPTO for U.S. Appl. No. 09/685,697 mailed Jun. 26, 2006, 8 pgs.
Office Action Summary from USPTO for U.S. Appl. No. 09/685,697 mailed Apr. 10, 2007, 9 pgs.
Office Action Summary from USPTO for U.S. Appl. No. 09/685,697 mailed Oct. 9, 2007, 11 pgs.
Office Action Summary from USPTO for U.S. Appl. No. 10/140,635 mailed Oct. 3, 2003, 9 pgs.
Office Action Summary from USPTO for U.S. Appl. No. 10/140,635 mailed Jul. 16, 2004, 11 pgs.
Office Action Summary from USPTO for U.S. Appl. No. 10/140,635 mailed Apr. 19, 2005, 11 pgs.
Office Action Summary from USPTO for U.S. Appl. No. 10/140,635 mailed Jan. 17, 2006, 13 pgs.
Office Action Summary from USPTO for U.S. Appl. No. 10/140,635 mailed Sep. 20, 2006, 15 pgs.
Office Action Summary from USPTO for U.S. Appl. No. 10/140,635 mailed Jun. 21, 2007, 15 pgs.
International Search Report for PCT/US2008/054987 filed on Feb. 26, 2008, and mailed on Oct. 8, 2008, 2 pgs.
Written Opinion of the International Searching Authority for PCT/US2008/054987 filed on Feb. 26, 2008, and mailed on Oct. 8, 2008, 9 pgs.
International Search Report and Written Opinion for PCT/US09/48577, International filed Jun. 25, 2009, mailed from ISA Aug. 7, 2009, 9 pgs.
Office Action for U.S. Appl. No. 12/268,963, filed Nov. 11, 2008, mailed from USPTO on Jul. 29, 2011, 18 pgs.

DIAGNOSTIC AND INTERVENTION TOOLS FOR EMERGENCY MEDICAL DISPATCH

RELATED APPLICATIONS

This application is a continuation of U.S. patent application Ser. No. 11/818,181, filed Jun. 13, 2007, entitled, "Diagnostic and Intervention Tools for Emergency Medical Dispatch," now issued as U.S. Pat. No. 7,645,234, which is hereby incorporated by reference in its entirety.

TECHNICAL FIELD

This invention relates to computer systems and methods for providing medical protocol interrogation for instructions and emergency dispatch. More specifically, the invention is directed to computer implemented tools to assist in the interrogation.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION

Figure 1:
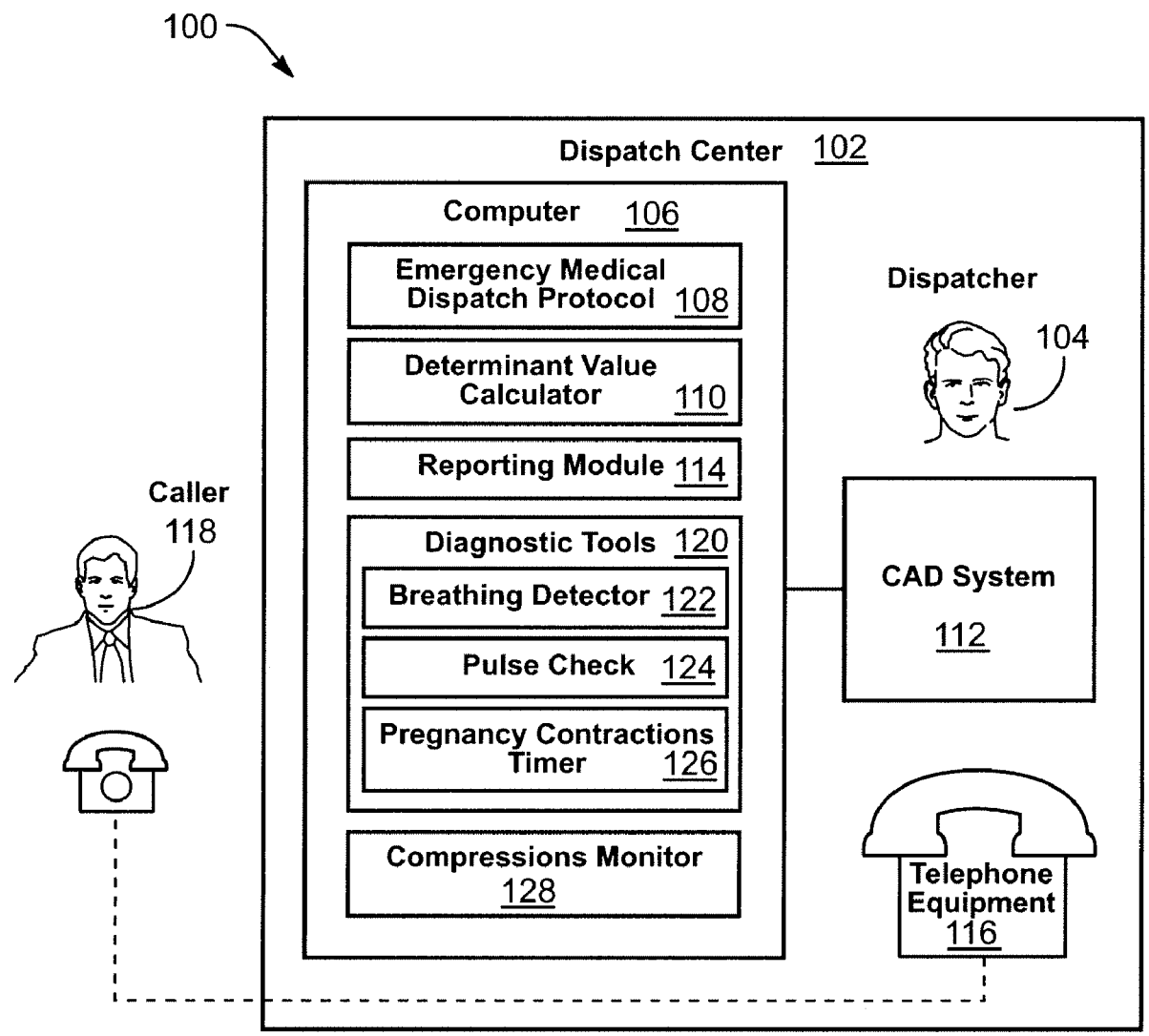
FIG. 1 is a block diagram of an embodiment of an emergency medical dispatch system.

The embodiments of the disclosure will be best understood by reference to the drawings, wherein like parts are designated by like numerals throughout. It will be readily understood that the components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified.

In some cases, well-known features, structures or operations are not shown or described in detail. Furthermore, the described features, structures, or operations may be combined in any suitable manner in one or more embodiments. It will also be readily understood that the components of the embodiments as generally described and illustrated in the figures herein could be arranged and designed in a wide variety of different configurations.

Several aspects of the embodiments described will be illustrated as software modules or components. As used herein, a software module or component may include any type of computer instruction or computer executable code located within a memory device and/or transmitted as electronic signals over a system bus or wired or wireless network. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

An emergency medical dispatch system disclosed herein may be computer-implemented in whole or in part on a digital computer. The digital computer includes a processor performing the required computations. The computer further includes a memory in electronic communication with the processor for storing a computer operating system. The computer operating systems may include MS-DOS, Windows, Unix, AIX, CLIX, LINUX, QNX, OS/2, and Apple. Alternatively, it is expected that future embodiments will be adapted to execute on other future operating systems. The memory also stores application programs including a Computer Aided Dispatch (CAD) program, an emergency medical dispatch protocol, and a user interface program, and data storage. The computer further includes an output device, such as a display unit, for viewing the displayed instructions and inquiries and as a user input device for inputting response data.

Referring to FIG. 1, one embodiment of a computer-aided medical dispatch system 100 is shown. At a dispatcher center 102, a dispatcher 104 operates a computer 106 that executes an emergency medical dispatch protocol 108 to enable the dispatcher to rapidly and consistently address a medical emergency. The emergency medical dispatch protocol 108 provides a logic tree with questions, possible responses from a caller, and instructions to a caller. The responses may route to subsequent questions and/or instructions to the caller. The responses are processed according to predetermined logic to both provide the correct emergency medical dispatch response and the appropriate doctor-approved post-dispatch instructions to the call taker before professional help arrives. Exemplary embodiments of such medical dispatch protocols are disclosed in U.S. Pat. Nos. 5,857,966, 5,989,187, 6,004, 266, 6,010,451, 6,053,864, 6,076,065, 6,078,894, 6,106,459, 6,607,481, and 7,106,835 which are incorporated herein by reference.

The computer 106 operates a determinant value calculator 110 to calculate a determinant value from the caller's responses to protocol questions. The computer 106 presents the determinant value to generate an appropriate emergency response. Since the questions asked and the recommendations that are made deal directly with life and death decisions, the protocols used shall have passed through a rigorous medical review by a panel of doctors and EMS public safety experts who specialize in emergency medicine, and dispatch procedures.

Since many calls for medical service are not true medical emergencies, it is important to prioritize the calls in several ways. First, calls that are true emergencies should be dispatched first. Second, if an agency has units with different capabilities, the more severe medical problems should receive the more advanced units. And finally, if lights-and-siren are not needed from a medical standpoint, they should not be used, thereby increasing the safety of all those on the road and in the emergency vehicles. While many medical calls are not true emergencies, all situations can benefit from medical evaluation and instruction. Prior to the arrival of professional help on-scene, the dispatch system provides instructions that are appropriate to the type of call, from minor lacerations to someone who is not breathing.

The determinant value provides a categorization code of the type and level of the incident, the code is provided to a Computer Aided Dispatch (CAD) system 112, which is a tool used by dispatchers to track and allocate emergency response resources, for processing. The CAD system 112 may operate in whole or in part on a separate computer in communication with computer 106. The primary information used in this task is location information of both the incident and units, unit availability and the type of incident. CAD systems may use third party solutions, such as E-911, vehicle location transponders and mobile data terminals for automating the location and availability tasks.

The computer 106 may include a reporting module 114 to statistically measure the performance of individual staff and overall center performance. These statistics include protocol compliance rates, call processing statistics, and peer measurements.

The dispatch center 102 includes telephony equipment 116 to answer emergency calls. A call into the dispatch center 102 from a caller 118 initiates creation of a medical call incident. The dispatcher 104 identifies the call as requiring an emergency medical dispatch, and the emergency medical dispatch protocol 108 is accessed. Some protocol questions are readily answered, whereas others are more difficult. Certain diagnostic inquiries may be difficult for the untrained caller to determine. The protocol 108 may provide instructions that are expertly drafted to assist a novice caller in diagnosing a patient's condition. The protocol 108 may also provide expertly drafted first aid instructions to assist a patient prior to the arrival of emergency responders.

In addition to instructions, the medical dispatch system 100 may provide computer-implemented diagnostic tools 120. The diagnostic tools 120 may be stored in the memory of the computer 106 and initiated and executed as required. The diagnostic tools 120 may be embodied as computer executable software applications and associated data. The protocol 108 may call on a diagnostic tool 120 to assist in an interrogatory and may route to a diagnostic tool 120 when needed. The diagnostic tools 120 allow a dispatcher 104 to provide consistent, expert advice to assist a caller in determining a vital sign.

The medical dispatch system 100 may automatically, i.e., without dispatcher intervention, initiate a diagnostic tool 120. This may occur when the emergency medical dispatch protocol 108 arrives at such a diagnosis step and initiates a corresponding diagnostic tool 120. The system 100 may also allow the dispatcher 104 the option to call upon a diagnostic tool 120 as desired. Icons may be displayed in a tool bar, or other convenient location on a user interface to allow the dispatcher 104 to initiate a corresponding diagnostic tool 120.

In determining vital signs, the diagnostic tools 120 are computer implemented software modules to provide consistent instruction and reliable timing. One of the benefits of the diagnostic tools 120 is the computer-aided timing of techniques to determine the vital signs. In highly stressful conditions, the diagnostic tools provide a necessary resource to reading critical signs.

Diagnostic tools 120 discussed herein include a breathing detector 122, pulse check 124, a pregnancy contractions timer, and a CPR compressions monitor 126. The diagnostic tools 120 are each discussed in reference to figures of graphical user interfaces that exemplify certain embodiments. One of skill in the art will appreciate that such interfaces may be implemented and designed in various ways and still be within the scope of the invention.

Figure 2A:
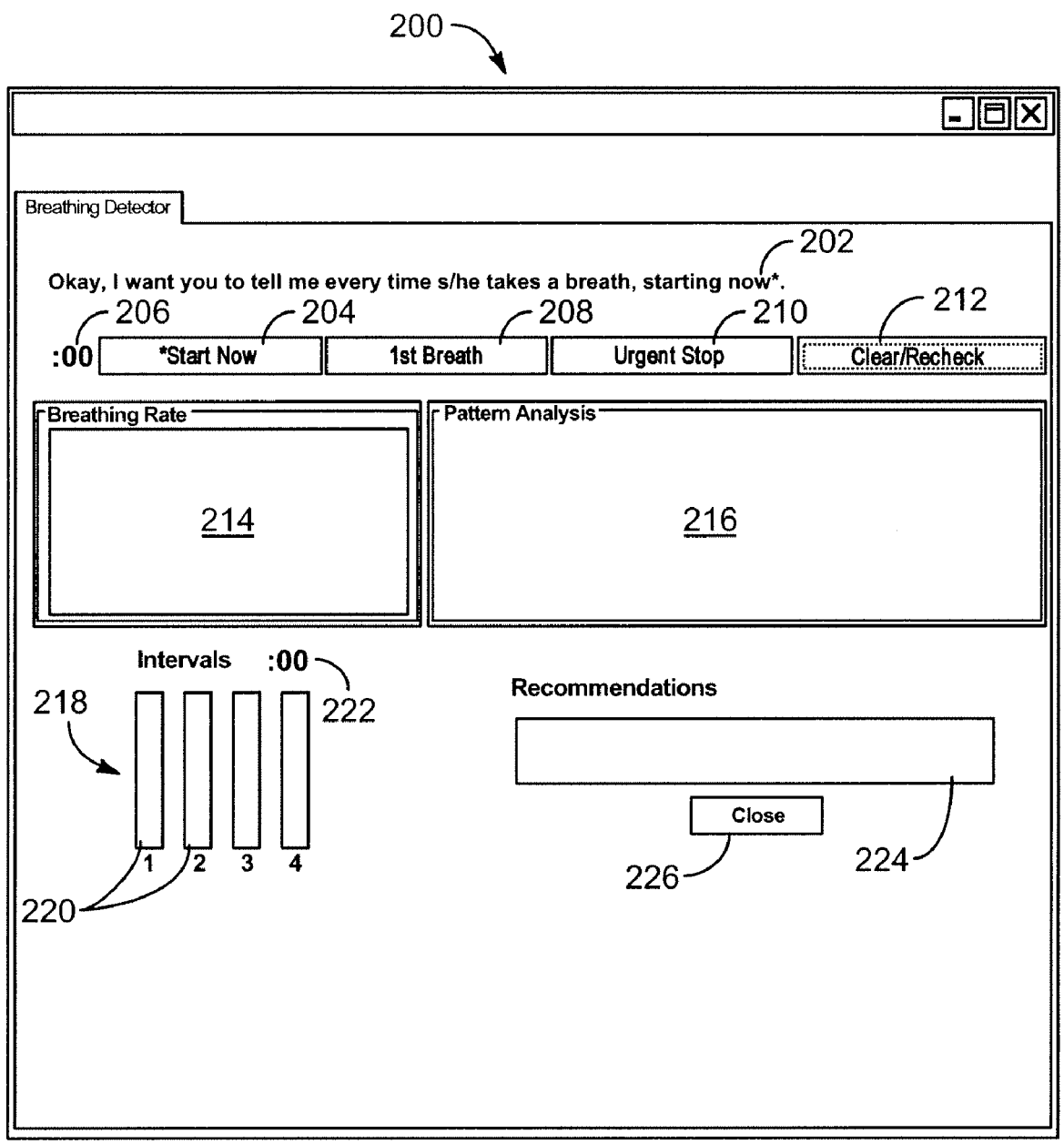
FIGS. 2A-2F illustrate an embodiment of an interface of a breathing detector tool.

Referring to FIG. 2A, an embodiment of a graphical user interface 200 for a breathing detector is shown. The interface 200 may include instructions 202 that the dispatcher 104 reads to the caller 118. The instructions 202 require that the caller 118 indicate each time a patient takes a breath starting immediately. The interface 200 may include a start button 204 to initiate the detection process. The dispatcher 104 clicks on the start button 204 which starts a timer 206. The timer 206 records the entire time of the detection process.

The interface 200 includes a breath button 208 which the dispatcher 104 clicks each time the caller indicates that a breath is taken. Initially, the breath button 208 may state "$1^{st}$ breath" to indicate the first breath of a patient. After clicking once, the breath button 208 may then state "$2^{nd}$ breath" and so forth to indicate the number of breaths. The interface 200 may include an urgent stop button 210 to terminate the detection process. The interface 200 further includes a clear/recheck button 212 to clear the received data and begin the detection process again. A breathing rate field 214 indicates breaths per minute based on breathing intervals. A pattern analysis field 216 provides a determined average breathing rate.

A bar chart 218 is provided which provides feedback on breathing intervals. Each bar 220 corresponds to a breathing interval and indicates the length of the interval. An interval timer 222 records the duration of the present interval. The interval timer 222 is reset each time a breath is recorded to then illustrate the duration of the next interval. As illustrated, four breathing intervals may be recorded for a detection process. The interface 200 includes a recommendations field 224 which displays recommendations and instruction generated by the breathing detector 122 upon termination of the process.

In the illustrated embodiment, a dispatcher 104 may click on the start button to initiate 204 once and the breath button five times to define four intervals. After reviewing the recommendations field 224, the dispatcher 104 may act immediately to generate a dispatch response. A dispatcher 104 may also return to the protocol 108 and enter a result of the detection process which will affect protocol outcome. Thus, the resulting determinant value may be based on the outcome of the detection process. In one embodiment, a determinant value may be automatically generated based on the outcome of the detection process.

The interface 200 may also include a close button 226. When operated, the close button terminates execution of the breathing detector 122. The dispatcher 104 may then return to the protocol 108.

Figure 2B:
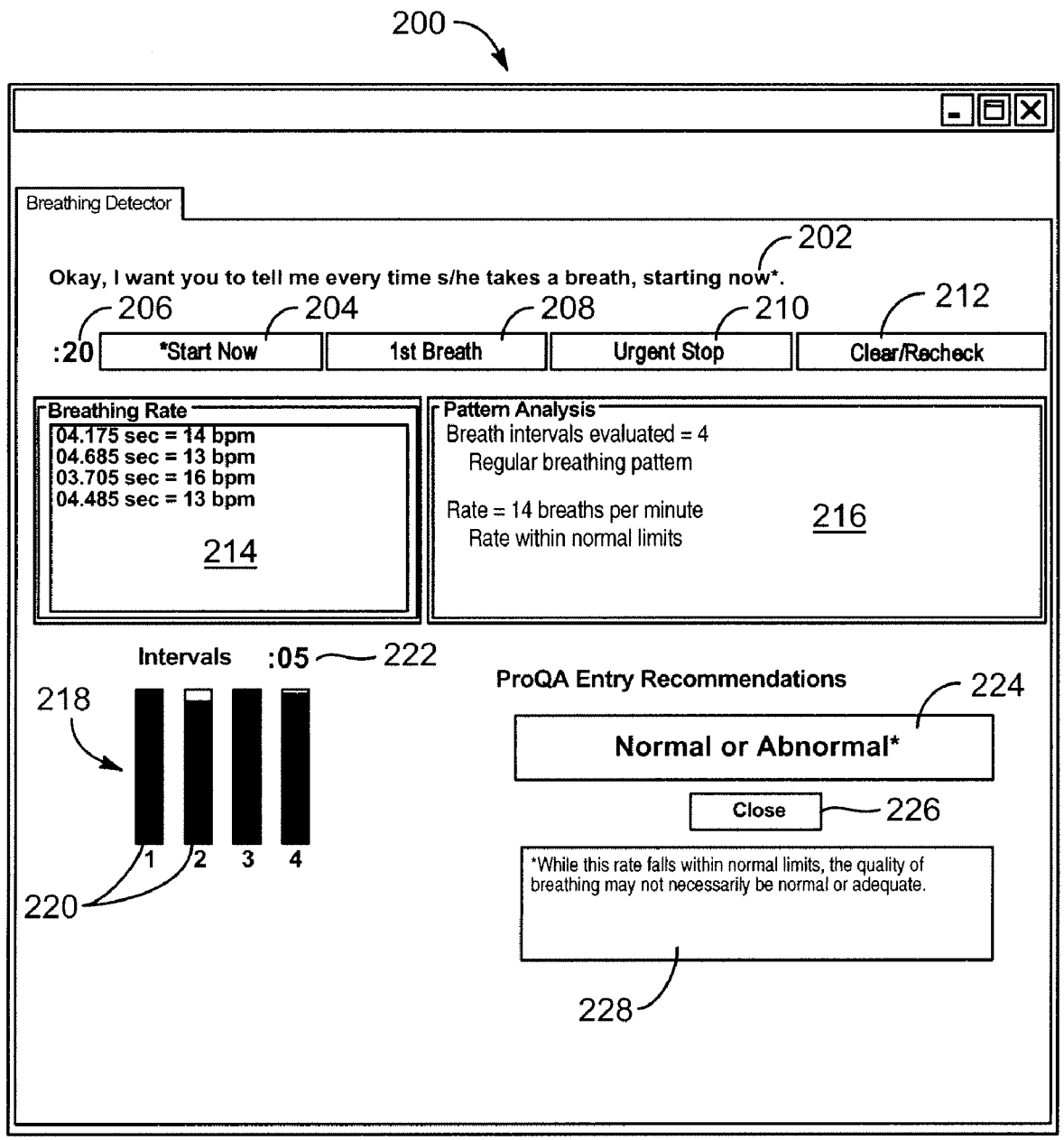

FIGS. 2B through 2E illustrate different results of a detection process performed by the breathing detector. In FIG. 2B, the timed values of different intervals are shown are shown in field 214 with corresponding, approximate breath-per-minute rates. An average breathing rate based on the breath intervals is displayed in pattern analysis field 216. The pattern analysis field 216 may also indicate that a breath rate is within normal limits. Each bar 220 may be filled to a level corresponding to an interval value. A bar 220 may be filled with a color indicating whether an interval is acceptable or troubling. For example, a bar 220 may have a fill color of red for dangerous, yellow for troubling, or green for acceptable. The recommendations field 224 provides a result of the detection process. The recommendations field 224 may be filled with color to indicate a danger level. As shown, the breathing is considered normal or possibly abnormal depending on the conditions. The interface 200 may also display recommendation instructions 228 which clarify the provided recommendation.

Figure 2C:
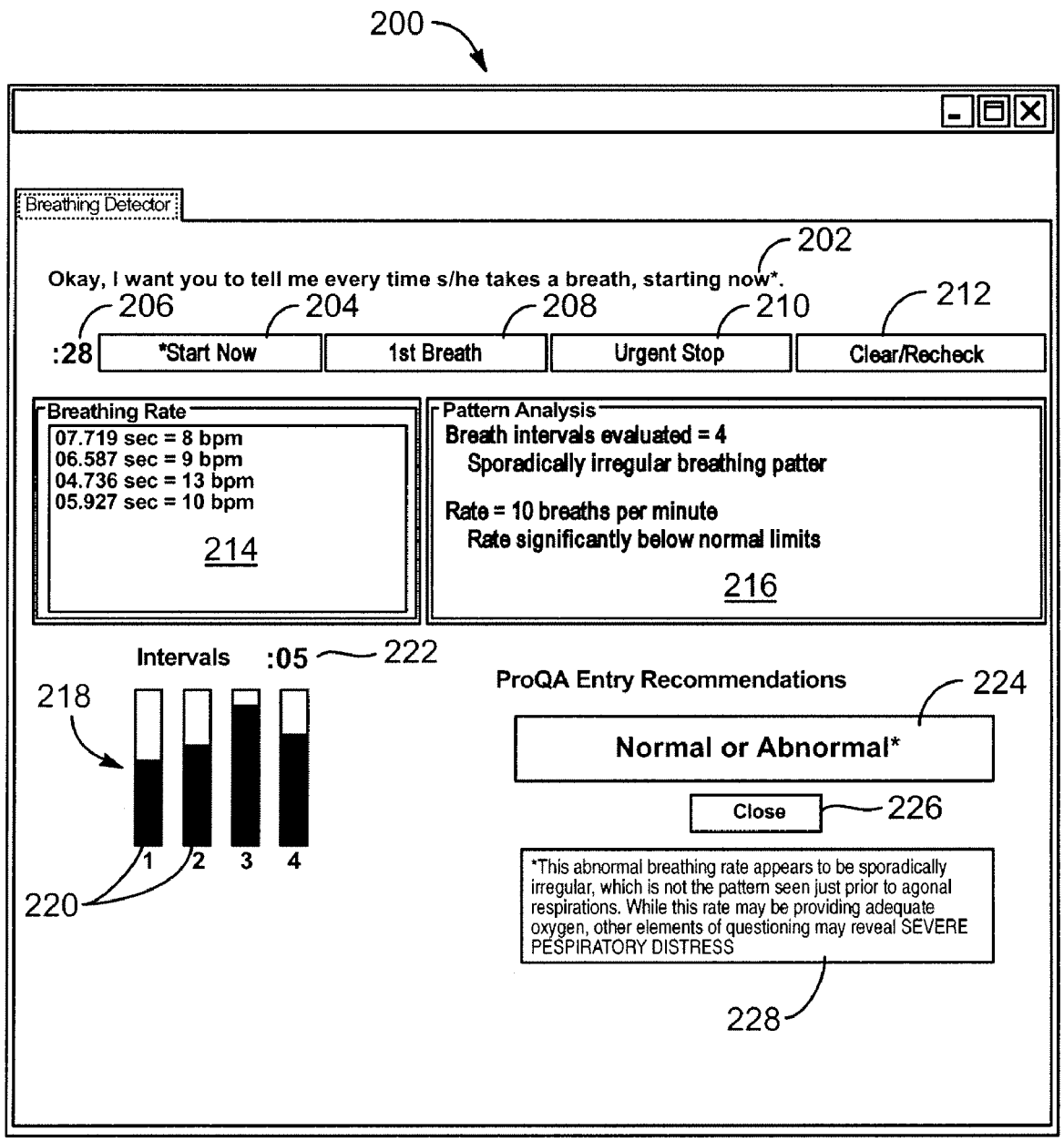

FIG. 2C illustrates a breathing pattern with irregularly spaced breathing intervals and with a breathing rate that falls below acceptable limits. The spacing and rate used by the breathing detector 122 are predetermined by experts to provide consistency and reliability. The recommendations field 224 outputs an abnormal or irregular indication. The instructions 228 provide further information about the result and the patient's condition. The result of this detection process will likely result in a higher priority for an emergency medical response.

Figure 2D:
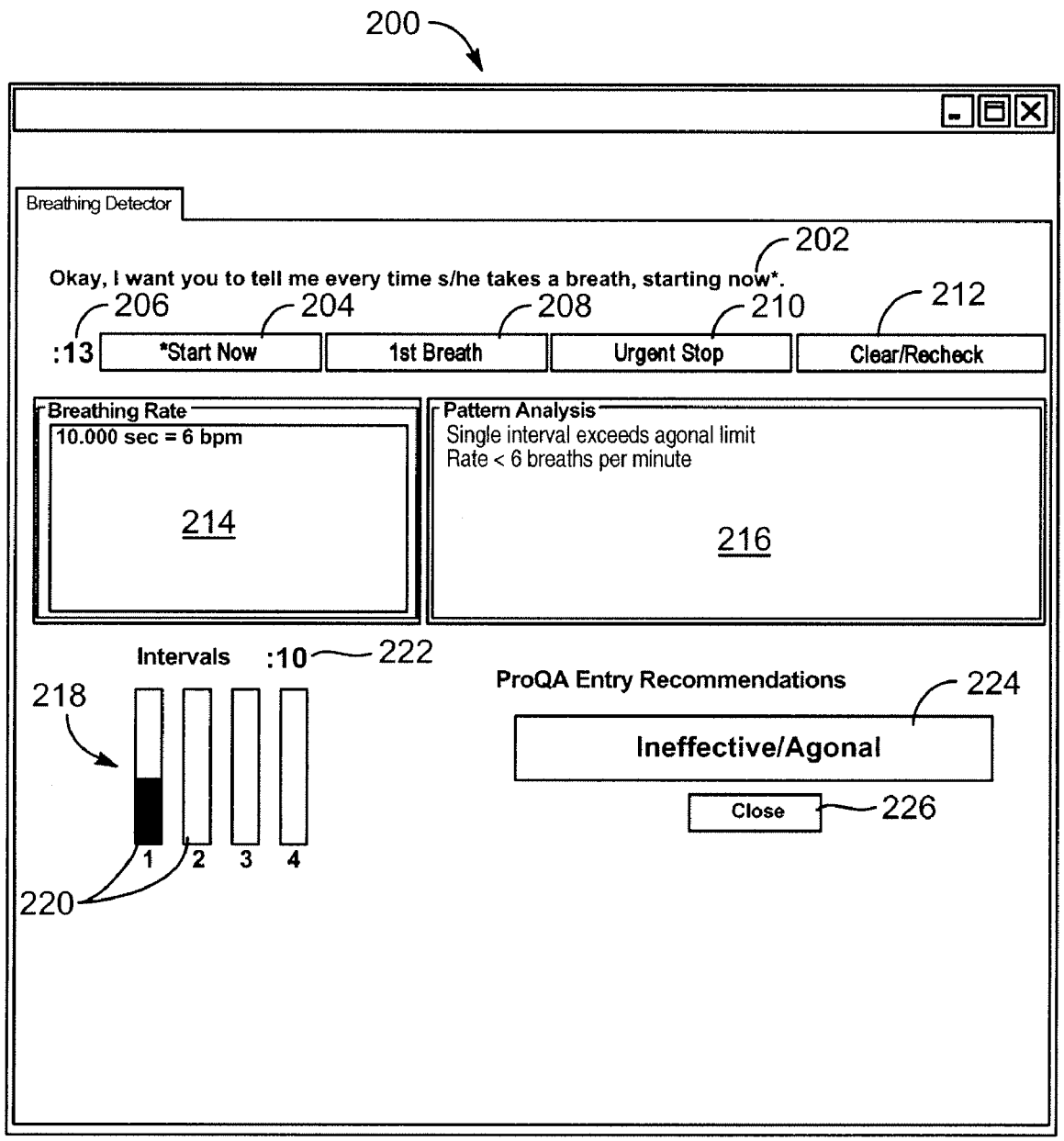

FIG. 2D illustrates a breathing pattern where only one interval is recorded. If any breath interval extends too long, the breathing detector 122 may interrupt the process and determine that breathing is ineffective. In the illustrated example, the second breath interval is at least ten seconds. Subsequent measurements of breath intervals are not needed, as the patient has exceeded an agonal limit. The recommendations field 224 states that breathing is ineffective or agonal, which will likely result in a high priority emergency medical response.

Figure 2E:
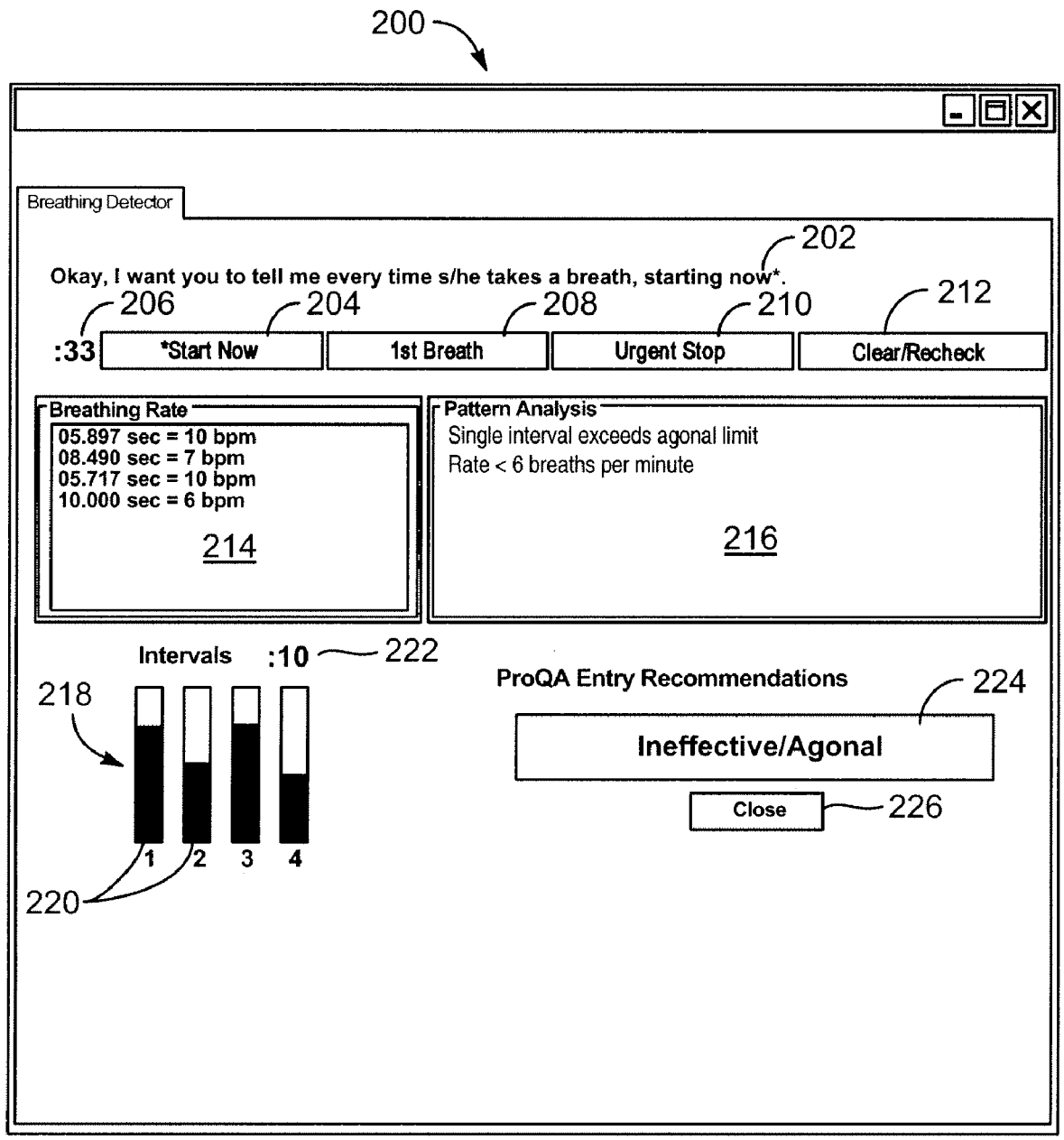

In FIG. 2E, another example of an ineffective or agonal breathing result is shown. All four breathing intervals are recorded, but the breath rate is below an acceptable range.

Figure 2F:
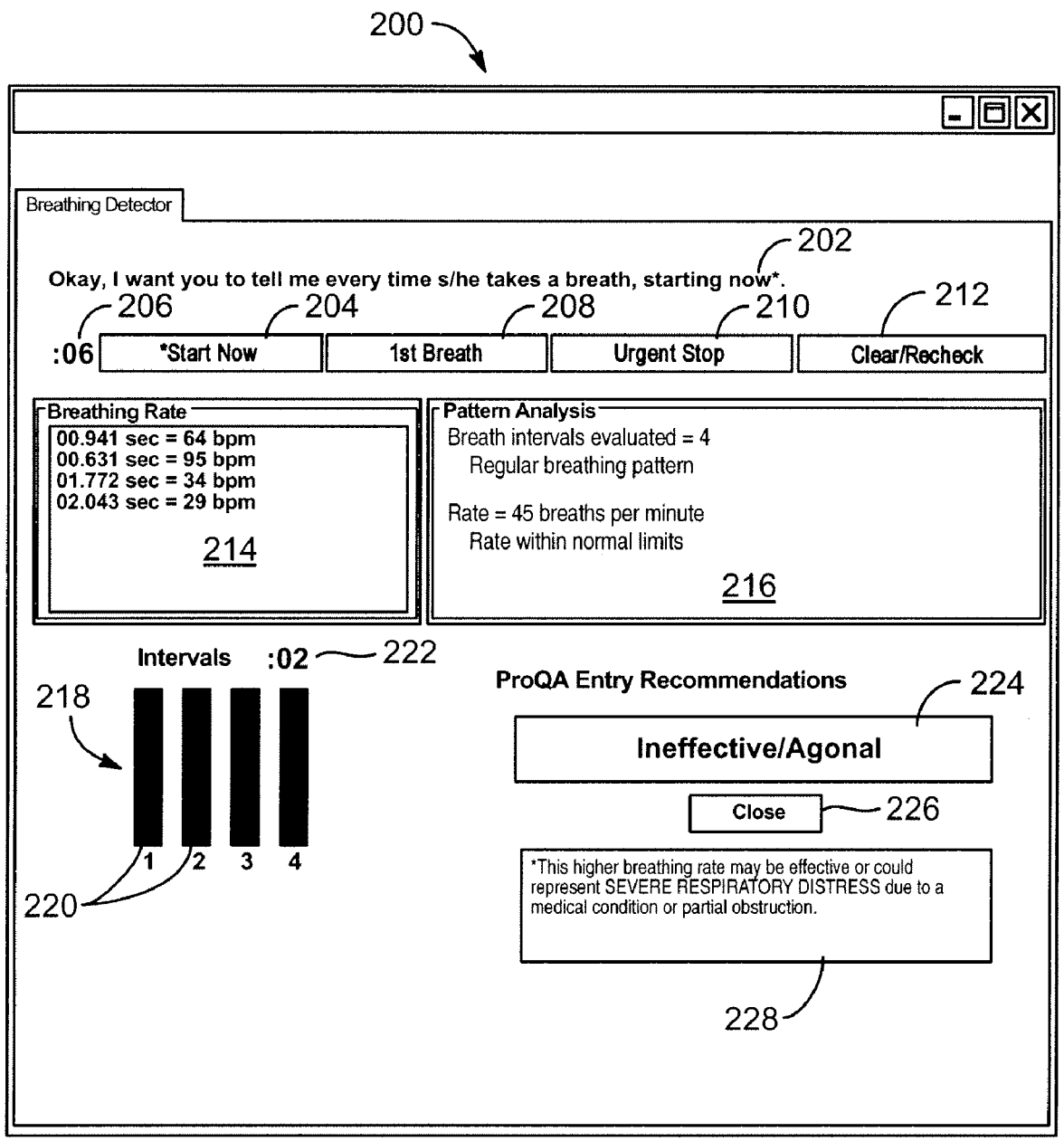

In FIG. 2F, an example of an excessive breath rate is shown. The recorded breath intervals provide a breath rate average of 45 breaths per minute. As this rate exceeds an acceptable range, the recommendations field 224 indicates an above normal rate.

Based on the results of the breathing detector, the priority of an emergency medical response is determined. The dispatcher 104 may also provide instructions to the caller 118 to assist a patient. These instructions may be referred to herein as post-dispatch, or pre-arrival instructions to indicate that they are given after responders are dispatched and/or before the responders arrive on the scene. In one example, where ineffective breathing is detected, a dispatcher 104 may provide intervention instructions to instruct a caller 118 to inspect the patient for any throat blockage. As can be appreciated, various intervention instructions may be provided to assist a patient.

Figure 3A:
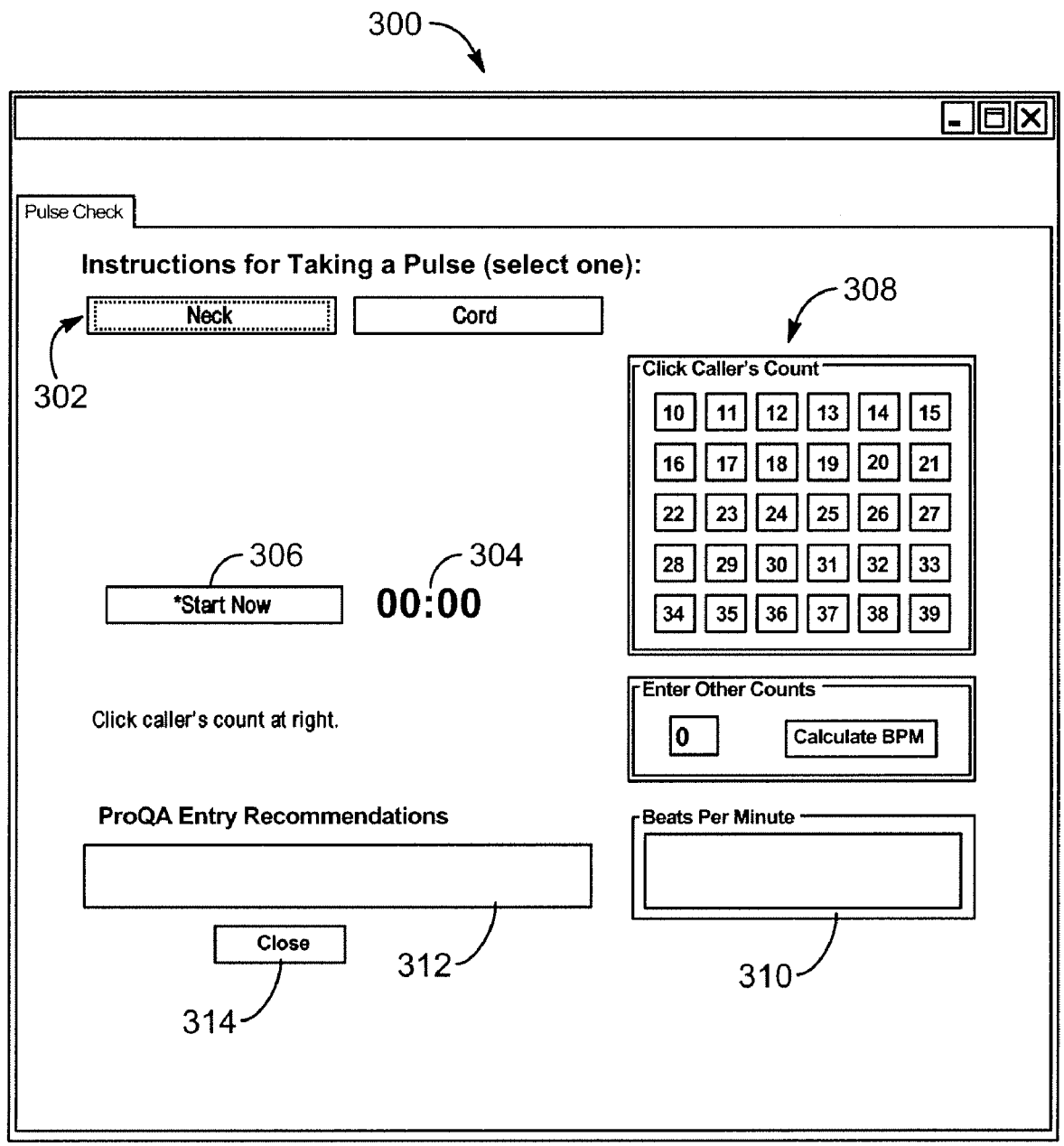
FIGS. 3A-3D illustrate an embodiment of an interface of a pulse check tool.

Referring to FIG. 3A, an embodiment of a graphical user interface 300 is shown for a pulse check 124. The interface 300 may provide instructions to assist a caller 118 in measuring a pulse rate. The caller 118 may or may not be the patient. Instruction buttons 302 may be provided to initiate display of pulse-taking instructions for the neck, umbilical cord, or some other body part. By clicking on an instruction button 302, pulse-taking instructions are displayed to the dispatcher 104.

The interface 300 provides a timer 304 which runs for a predetermined amount of time. In one embodiment, the timer runs for 15 seconds. A start button 306 is provided and, when clicked, begins the timer 304. Upon initiation, the dispatcher 104 instructs the caller 118 to begin counting pulses. During the time interval, the caller 118 counts the number of pulses. The interface 300 indicates to the dispatcher 104 when the time interval is expired. Upon expiration, the dispatcher 104 instructs the caller 118 to stop counting and asks for the final number.

A common count input field 308 is provided for the dispatcher 104 to enter the number of pulses provided by the caller 118. The illustrated field 308 allows a dispatcher 104 to click on the correct number. If the correct number is not shown in the input field 308, the field 308 allows for typed entry of the number of pulses as shown.

A beats-per-minute (BPM) field 310 displays the rate based on the Dispatcher's input to the count input field 308. The calculation is performed by the pulse check 124 based on the predetermined time interval. A recommendations field 312 displays a result of pulse check process based on the number of pulses inputted. A close button 314 closes the interface 300 and terminates operation of the pulse check 124.

Figure 3B:
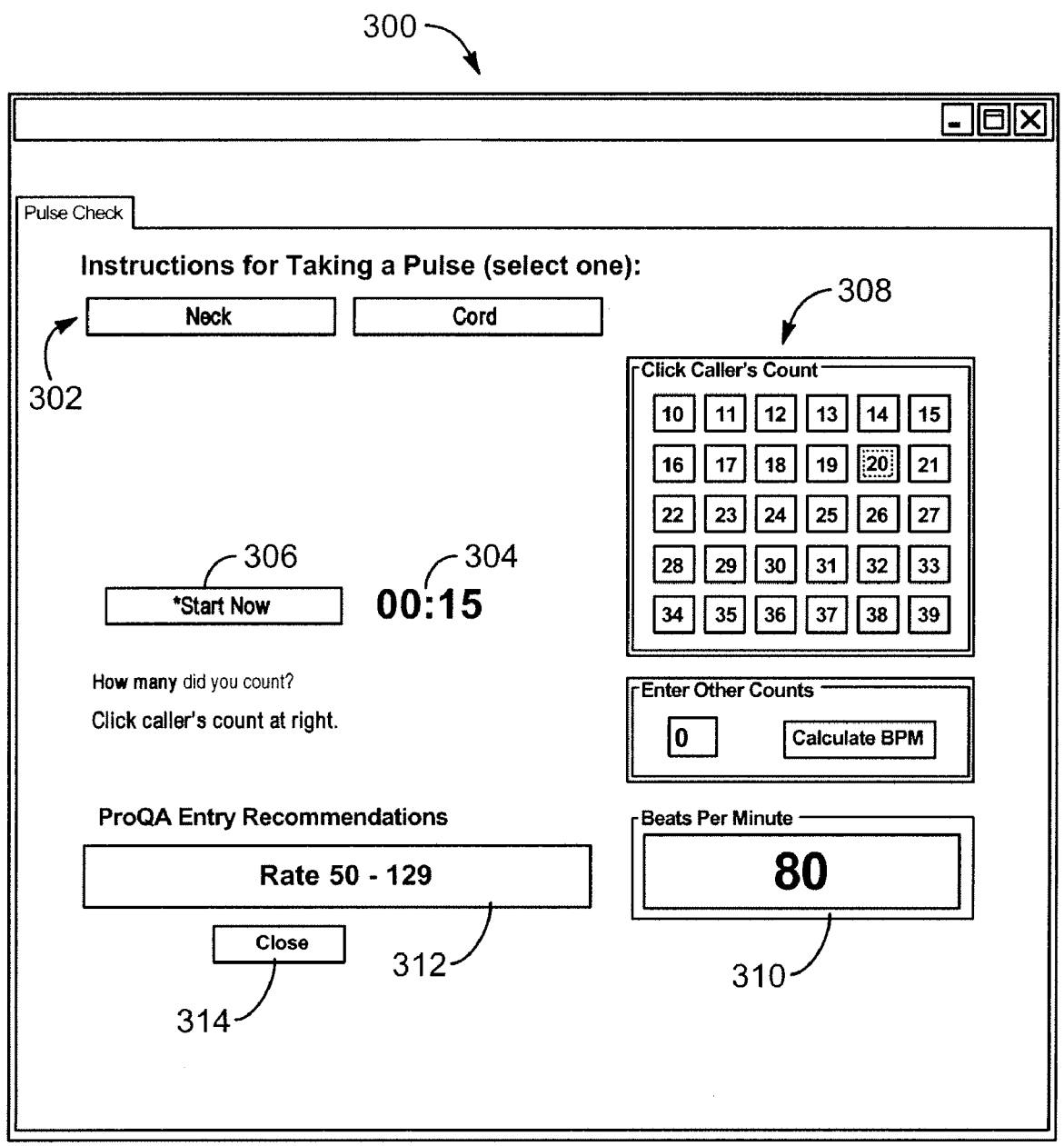
Figure 3C:
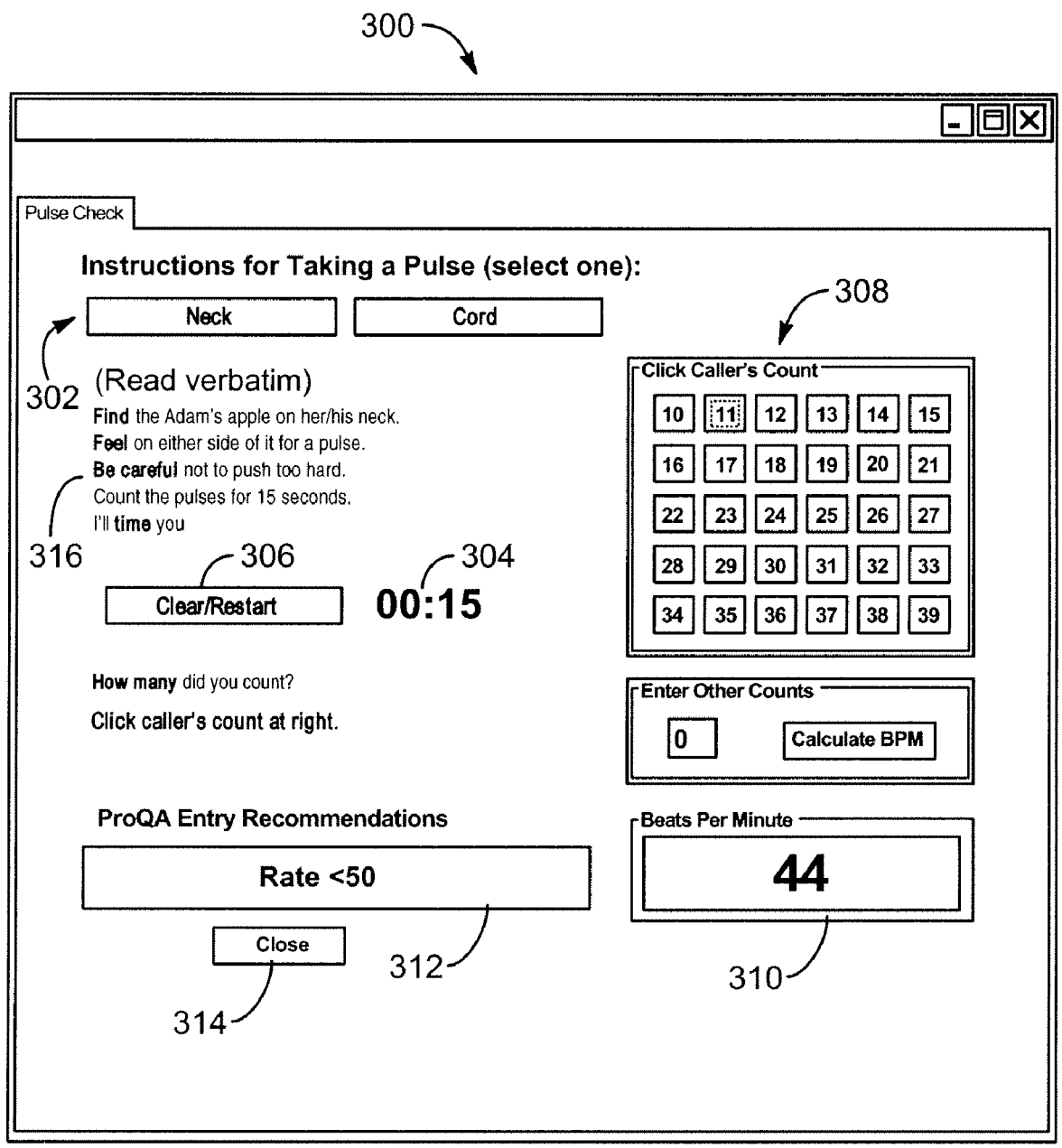
Figure 3D:
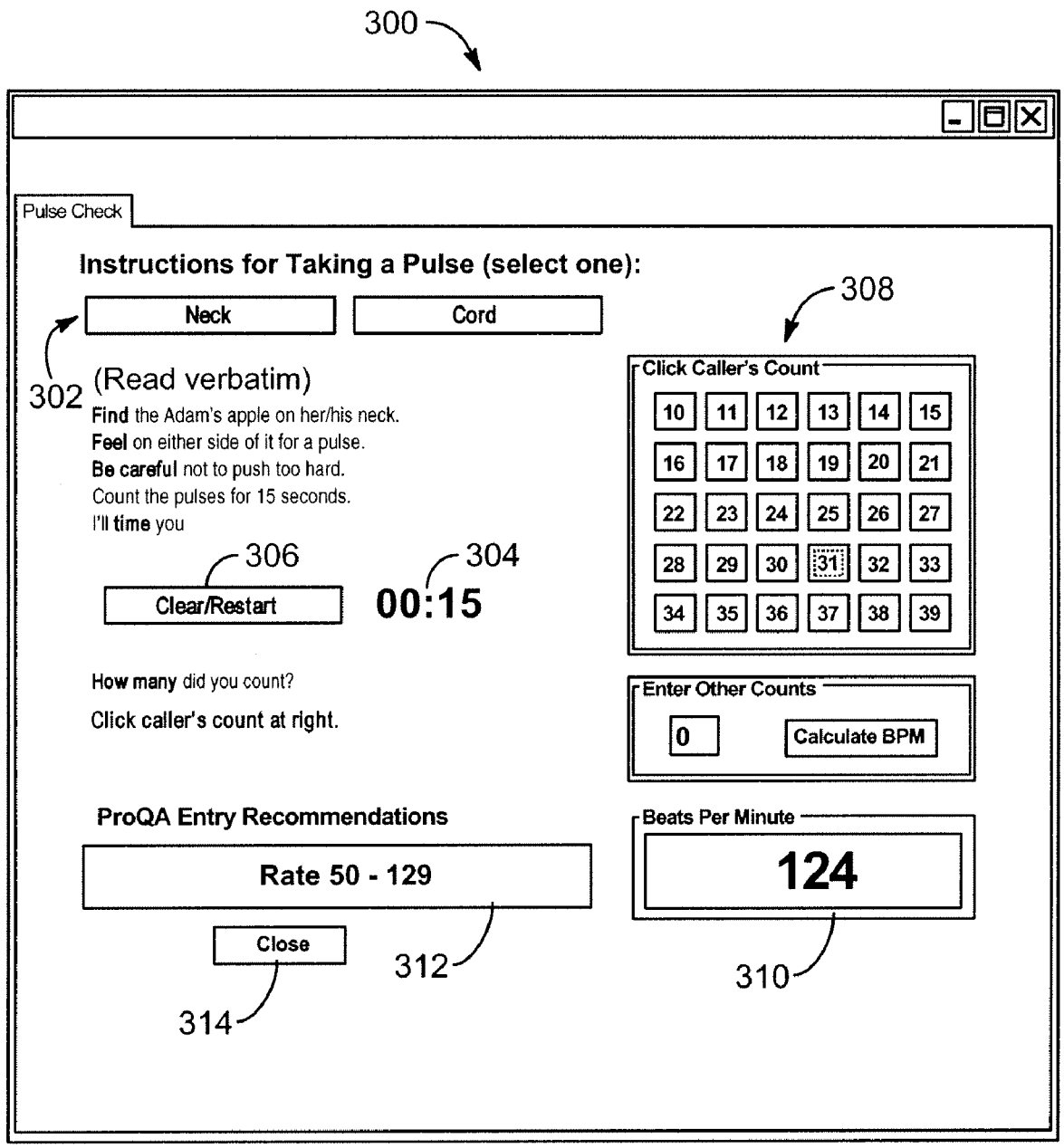

FIGS. 3B, 3C, and 3D illustrate different pulse rate results. In FIG. 3B, the timer 304 has run for 15 seconds which is its predetermined interval. The dispatcher 104 selects the number of pulses counted, which in this example is 20. Upon entering the number of pulses, the BPM field 310 displays the beats per minute. The recommendations field 312 provides a rate range which may be used to determine a determinant value for a priority in an emergency response. The illustrated range is acceptable and does not, by itself, indicate a medical issue.

In FIG. 3C, the dispatcher 104 has selected the "neck" instruction button 302 and corresponding instructions 316 are displayed to the dispatcher 104. The dispatcher 104 reads the instructions 316 to the caller 118 to assist in finding a pulse and measuring a rate. The timer 304 is shown as having run for 15 seconds. The count inputted into the count input field 308 is 11. The BPM field 310 returns with a rate, and the recommendation field 312 provides a resulting range. In the given example, the rate of 44 beats per minute is in a range that is low. After a result is provided, the start button 306 may display a clear/restart option to allow a repeat of the process to take a pulse.

The recommendation field 312 may be filled with a color to indicate whether or not the range is acceptable. The color indication assists the dispatcher 104 in quickly confirming a range and whether or not the rate is an issue in the medical emergency. As with the breathing detector 122, the pulse check 124 provides a result that may be used by the dispatcher 104 to determine a determinant value and/or set an emergency medical response priority. The result may also be automatically used by the calculator 110 in setting a determinant value.

In FIG. 3D, the timer 304 is shown as having run for 15 seconds. The count inputted into the count input field 308 is 31. The BPM field 310 returns with a rate of 124 beats per minute. The recommendation field 312 provides a resulting range. The rate may be provided to the protocol 108 and/or to emergency responders prior to their arrival.

Figure 4A:
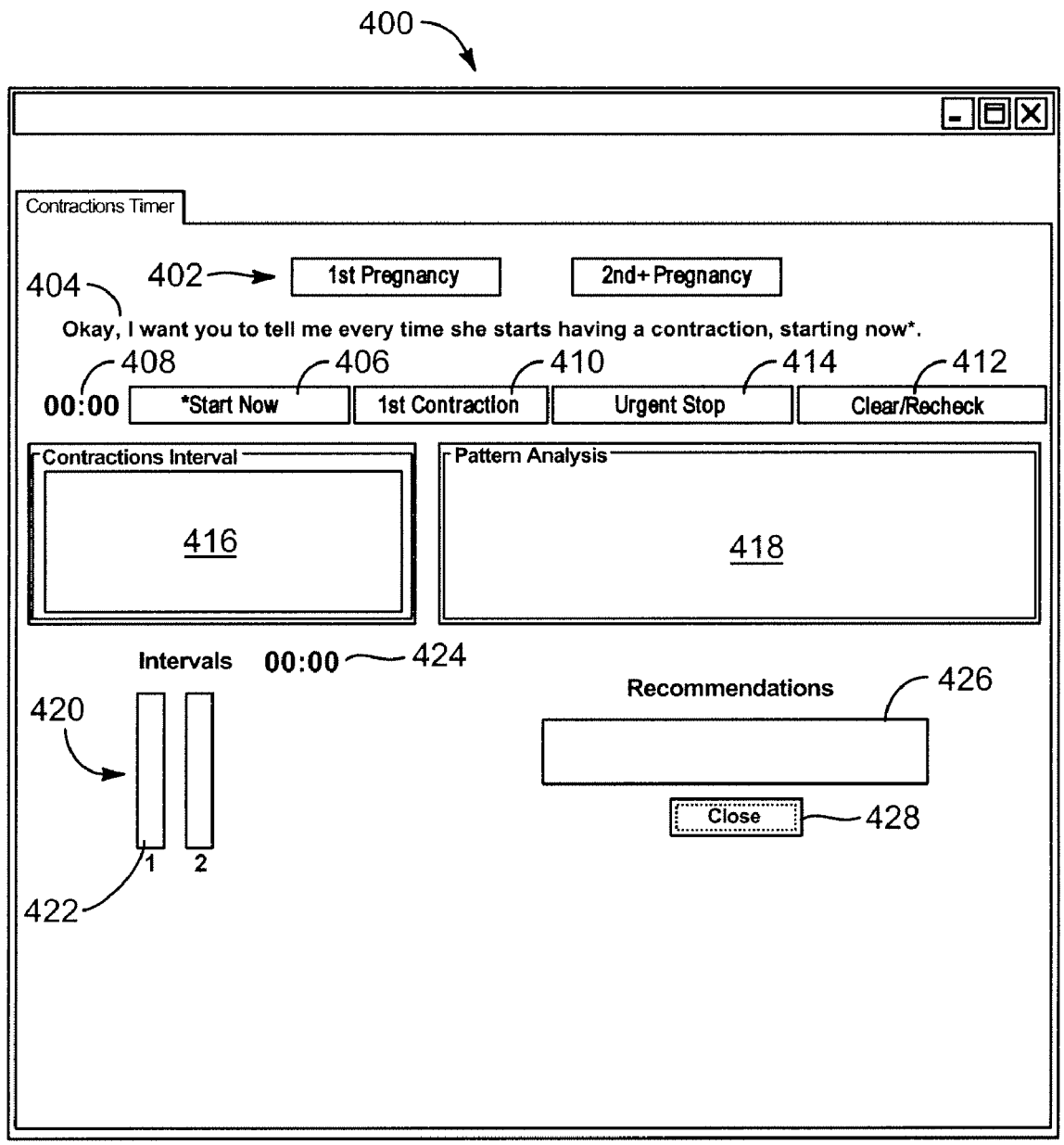
FIGS. 4A-4D illustrate an embodiment of an interface of a pregnancy contractions timer tool.

Referring to FIG. 4A, an embodiment of a graphical user interface 400 for a pregnancy contractions timer 126 is shown. The interface 400 includes a number input 402 to indicate the number of the current pregnancy. In the illustrated embodiment, the dispatcher 104 may select that this is either the first pregnancy or that the patient has had at least one previous pregnancy. The interface 400 may also include instructions 404 that the dispatcher reads to the caller 118 to assist in measuring contraction intervals. The interface 400 includes a start button 406 to begin a timer 408 and to initiate contraction timing. A caller 118 tells the dispatcher 104 each time a contraction occurs. The dispatcher 104 clicks a contraction button 410 when the dispatcher 104 is told of a contraction.

A clear/recheck button 412 allows the dispatcher 104 to terminate the timing process and begin again. An urgent stop button 414 may be provided to immediately terminate the process, close the interface 400, and return to the protocol 108. A contractions interval field 416 lists the duration of contraction intervals. A pattern analysis field 418 provides an average contraction rate. A bar chart 420 includes bars 422 with each bar indicating an interval between contractions. As illustrated, the number of bars and intervals to be recorded is two, although this number may be varied as desired. An interval timer 424 displays the time of the current interval. A recommendations field 426 displays a result after a predetermined number of intervals have been recorded. A close button 428 may be provided to terminate the pregnancy contractions timer 126 and close the interface 400.

Figure 4B:
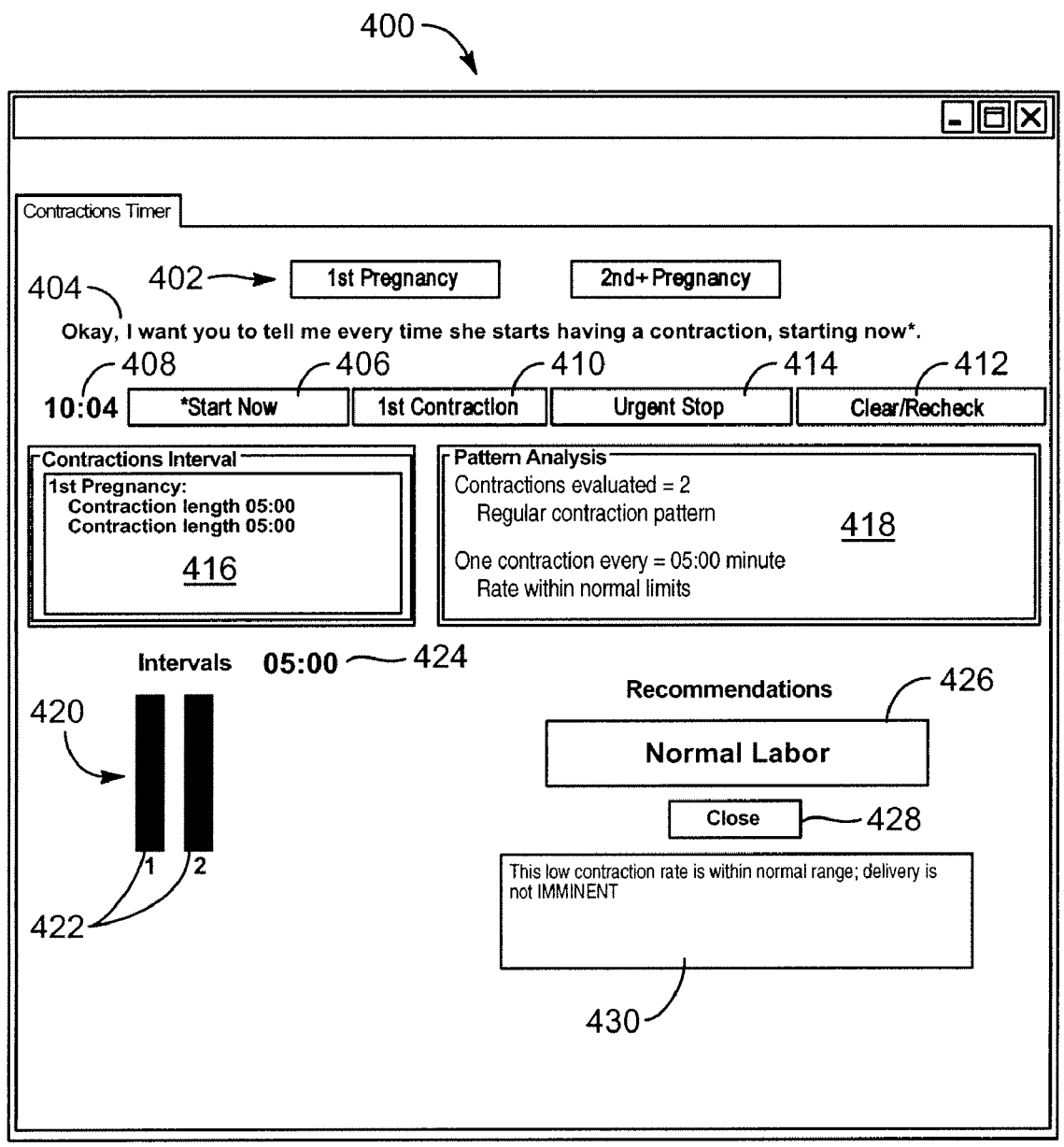

In FIG. 4B, two intervals between contractions have been recorded. As shown in field 416, the contraction intervals are at five minutes each. This is also indicated in the bar chart 420. The bars 422 may be filled to indicate the duration of an interval. The pattern analysis field 418 provides a contraction rate which is an average of the two intervals. The field 418 also indicates that this is a regular contraction pattern as the two intervals are similar in duration. The recommendation field 426 provides a result based on the contraction intervals. The result is determined by the monitor 128 to be a normal labor. The recommendation field 426 may also be filled with a color to indicate a time to deliver. The interface 400 may further provide result instructions 430 to clarify the provided result.

Figure 4C:
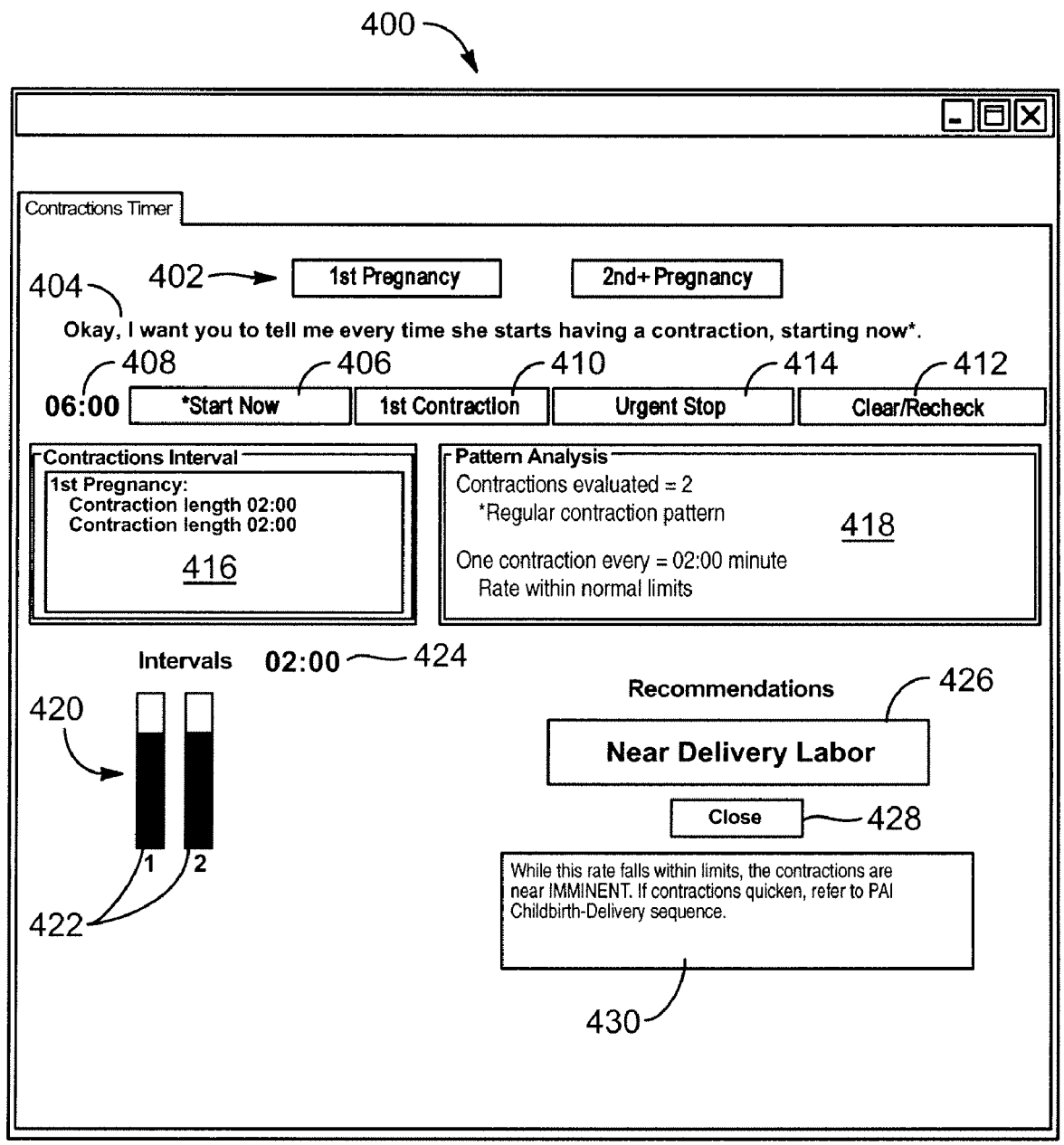

In FIG. 4C, the contraction intervals are at two minutes each. As can be appreciated, the contraction intervals may vary from one another, and those illustrated herein are for examples only. The contraction interval field 416, pattern analysis field 418, and bar chart 420 all reflect the measured contraction intervals. The recommendations field 426 displays a result that the patient is near delivery labor.

Figure 4D:
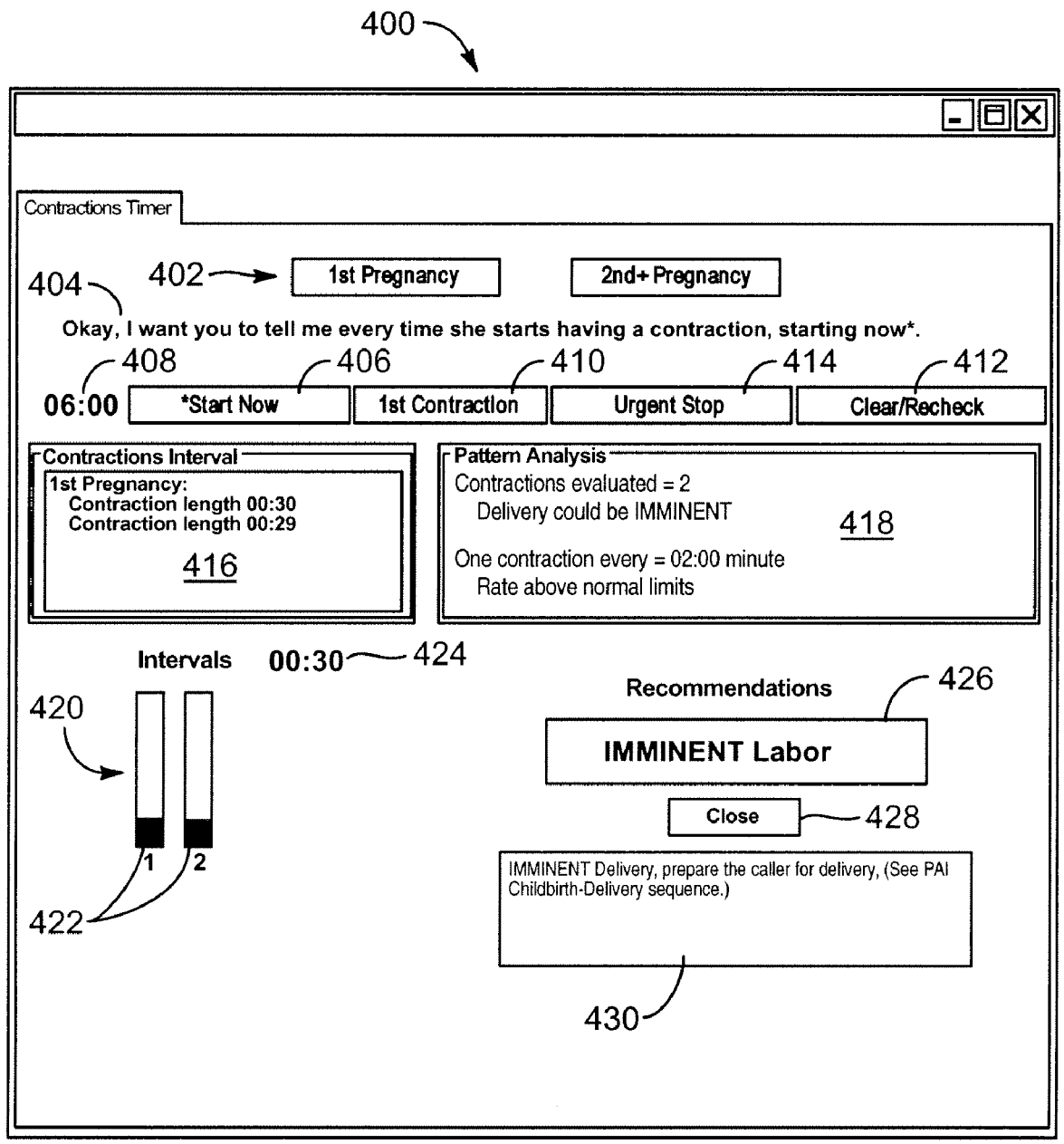

In FIG. 4D, the contraction intervals are at approximately 30 seconds. The fields 416, 418 and bar chart 420 display each interval length and an average of the two intervals. The recommendation field 426 displays the result that delivery is imminent. As can be expected, the results provided by the monitor 128 may be used to determine the priority of an emergency medical response and instructions to the caller 118 to assist the patient.

The diagnostic tools provide a reliable method for determining a time-based vital sign. The computer-operated timer ensures reliability which may not be provided by a caller inexperienced in measuring vital signs and faced with a highly stressful situation evaluated non-visually over the phone. Use of the diagnostic tools requires correspondence between a dispatcher and a caller to effectively take time-based measurements. As can be appreciated, reliable vital signs greatly enhances the entire emergency dispatch decision-making process and responder operation.

Referring once again to FIG. 1, the computer 106 used in the system 100 may further include an intervention tool to assist a caller 118 or other party in administrating aid to a patient. The intervention tool may be a compressions monitor 128 to assist in a CPR or like procedure. When a caller 118 indicates that a medical emergency requiring CPR intervention is occurring, the dispatcher 104 may initiate the compression monitor 128 to provide a timing guideline.

Figure 5A:
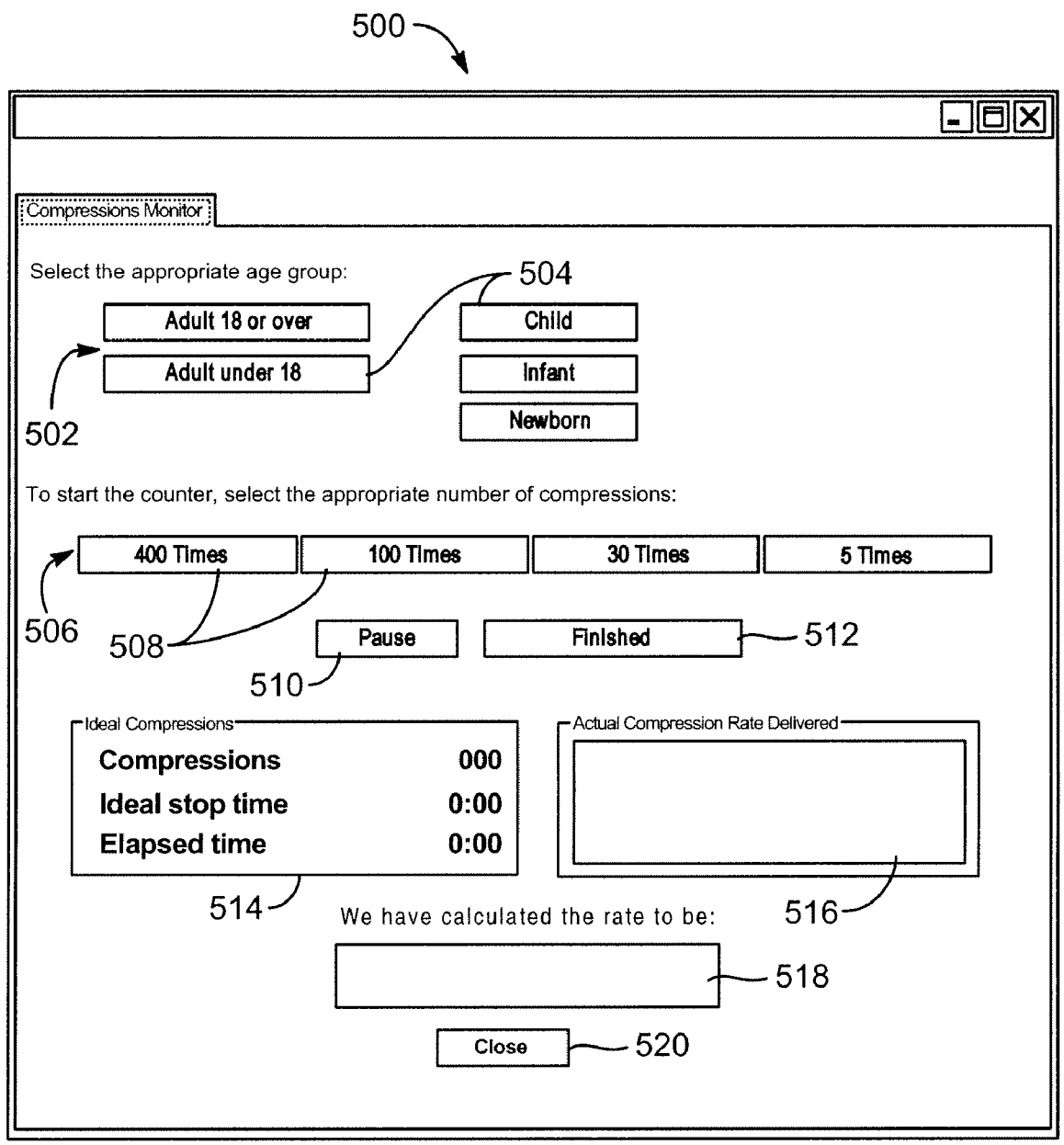
FIGS. 5A-5D illustrate an embodiment of an interface of a compressions monitor tool.

Referring to FIG. 5A, an embodiment of a graphical user interface 500 generated by the compressions monitor 128 is shown. The interface 500 includes an age input field 502 which may include a plurality of buttons 504 for a dispatcher 104 to select. Each button 504 corresponds to a different age or age group of a patient. Alternatively, the age input field 502 may allow the dispatcher 104 to type in an age or age group of the patient. The age of the patient is used by the compressions monitor 128 to determine an appropriate compressions rate.

The interface 500 also includes a compressions bar 506 which may include a plurality of compression buttons 508. Each compression button 508 corresponds to a predetermined number of compressions that are to be administered to the patient. The number of compressions may be listed on the corresponding button 508. Selecting a compression button 508 starts a timer of the compressions monitor 128, and administration of the selected number of compressions is to begin. In selecting the compression button 508, the dispatcher 104 tells the caller 118 to begin administering compressions. The interface 500 may alternatively provide a start button (not shown) to begin a timer for actual time to administer the compressions.

The interface 500 may include a pause button 510 that pauses the timer for any reason. The interface 500 includes a finished button 512 that terminates the timer. The finished button 512 is selected by the dispatcher 104 when the caller 118 indicates that the selected number of compressions is completed.

The interface 500 further includes an ideal compressions field 514 which may list the number of compressions administered, an ideal stop time to administer a selected number of compressions, and the actual time that elapsed to administer the compressions. The interface 500 may further include an actual compression rate field 516 to display a calculated compression rate. The interface 500 includes a recommendation field 518 which displays a result of the calculated compression rate. The recommendation field 518 may be filled with a color or highlighted to provide a visual indication about the compression rate. A close button 520 is provided to terminate the compressions monitor 128 and close the interface 500.

Figure 5B:
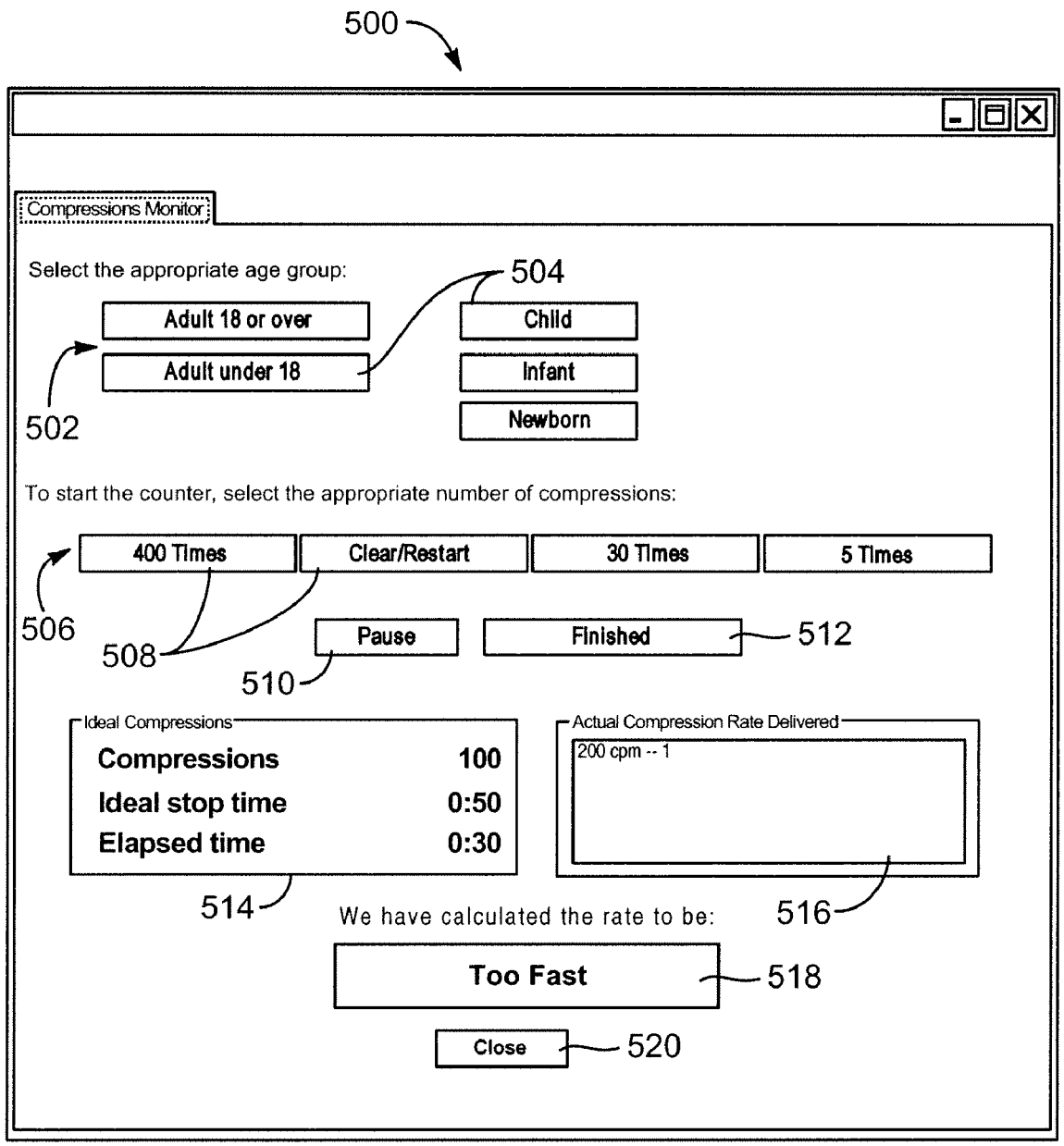

In FIG. 5B, a compressions button 508 corresponding to 100 compressions has been selected. As shown in the ideal compressions field 514, the ideal time was 50 seconds, but the actual time to complete 100 compressions was done in 30 seconds. The actual compression rate field 516 indicates a rate of 200 compressions per minute which is too fast. The recommendation field 518 displays a result of "too fast" to indicate that the caller 118, or other individual administering the compressions, is going too fast. The selected compressions button 508 may display a "clear/restart" label to indicate that selection will clear the timer, field 514, and the result to begin again. The field 516 may retain the compressions per minute to compare against the next process.

Figure 5C:
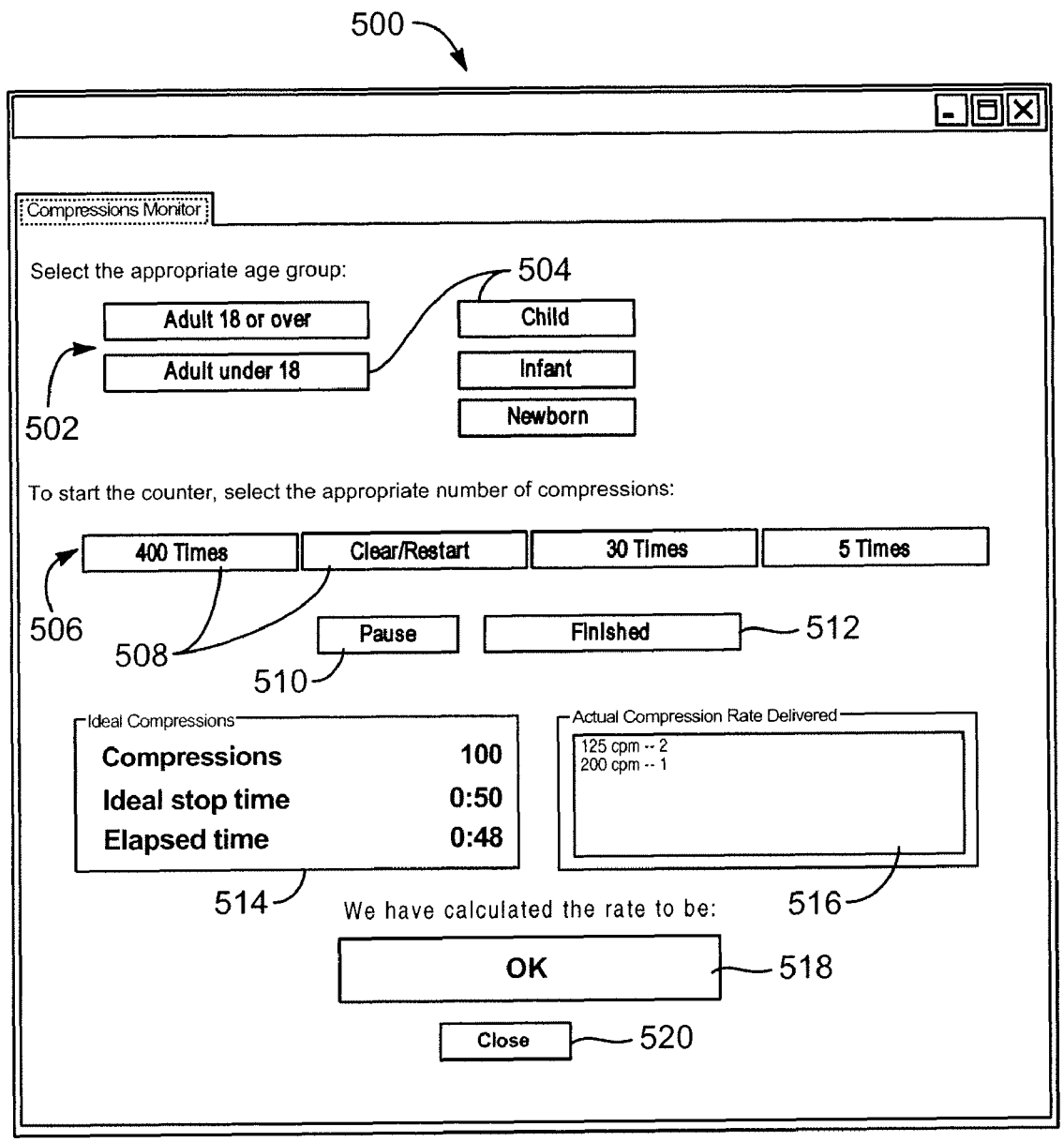

In FIG. 5C, the process is repeated for 100 compressions. As shown, the actual elapsed time in field 514 is 48 seconds. The actual elapsed time is not equal to the ideal time, but is close enough to be considered by the compressions monitor 128 to be acceptable. The compression rate is displayed in field 516 along with the previous compression rate. The recommendations field 518 displays the result to be "O.K."

Figure 5D:
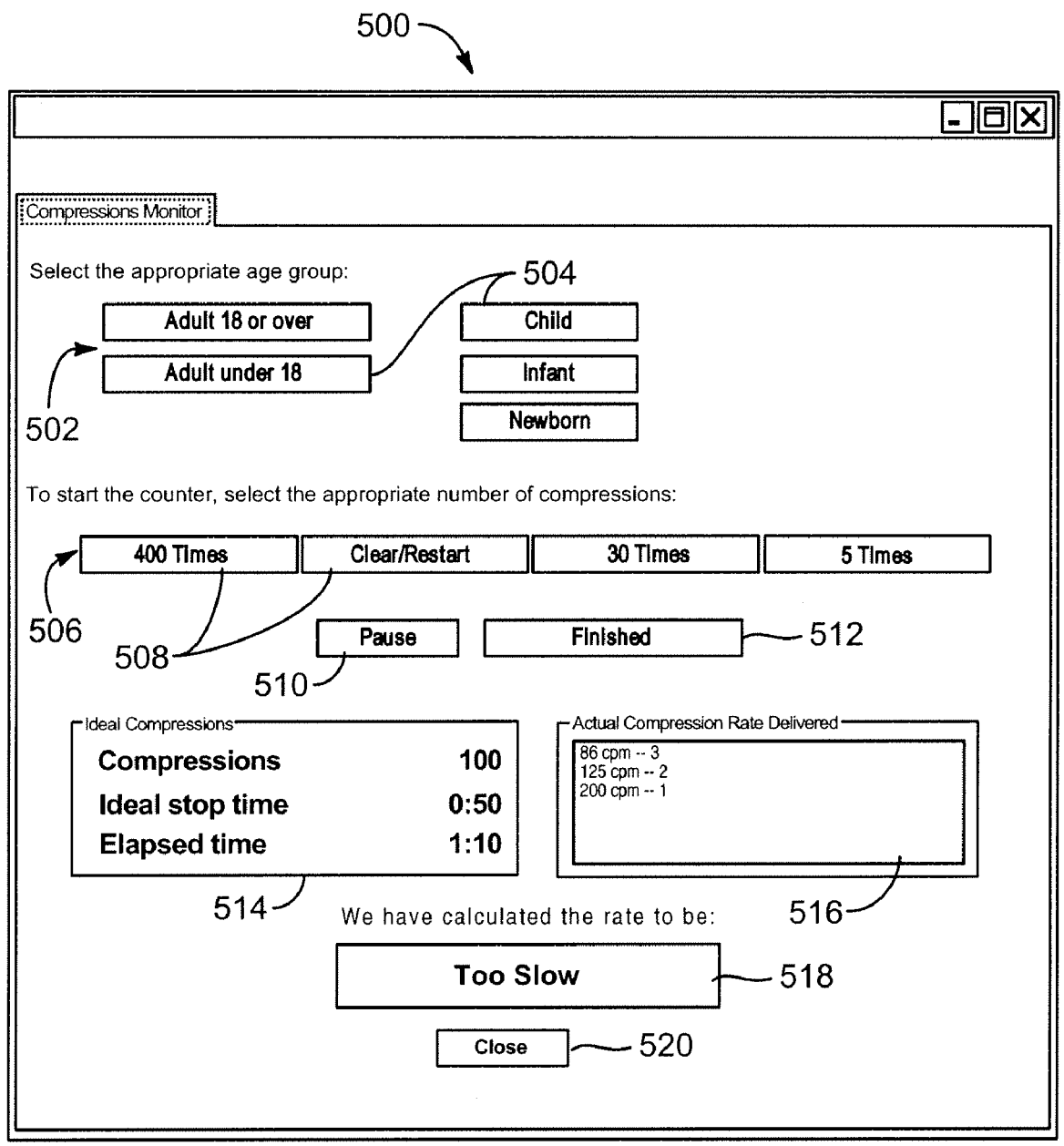

In FIG. 5D, the process is repeated again for 100 compressions. The elapsed time, shown in field 514, is one minute and ten seconds. The compression rate of 86 compressions per minute is displayed in field 516. This compression rate is displayed with the previous compression rates to provide comparison. The dispatcher 104 can thereby provide feedback to the caller 118 about the compression rate. As indicated in field 518, the compression rate is too slow.

The compressions monitor 128 provides a timer and feedback for each compression rate to improve intervention performance. A computer-implemented timer and a trained dispatcher 104 provide a stable measurement of a compression rate to improve performance. The dispatcher 104 and the caller 118 maintain communication to ensure proper start and stop times. In this manner, a CPR technique may be effectively administered to a patient prior to the arrival of emergency responders. Even an inexperienced caller 118, or other individual, may then administer compressions at a preferred and correct rate.

The diagnostic and intervention tools provide a user-friendly interface to assist the dispatcher in responding to an emergency call. The interface may include text, audio, video, and combinations thereof to assist a caller in finding vital signs and/or providing compressions in a CPR technique. The tools provide a timer for timing and recording body functions, such as breaths, pulses, and pregnancy contractions. The tools provide a timer for timing a CPR compression rate. Furthermore, all information taken by the tools may be stored by the system 100 and conveyed to the determinant value calculator 110, the reporting module 114, the CAD system 112 and to emergency responders. This information may be used to assist emergency responder prior to arrival. The tools greatly improve information collection and intervention for emergency medical response situations and will be an aid in saving lives.

While specific embodiments and applications of the disclosure have been illustrated and described, it is to be understood that the disclosure is not limited to the precise configuration and components disclosed herein. Various modifications, changes, and variations apparent to those of skill in the art may be made in the arrangement, operation, and details of the methods and systems of the disclosure without departing from the spirit and scope of the disclosure.

What is claimed is:

1. A computer implemented method performed entirely by a dispatch center computer system at a dispatch center to assist a dispatcher responding to a telephonic call from a caller regarding the medical condition of a patient to thereby enable determination of information about a vital sign of the patient without the assistance of medical equipment at a remote location of the caller and patient, the dispatcher to dispatch emergency medical responders to the remote location where the caller and patient are both present, the method comprising:
    the dispatch center computer system providing an emergency dispatch protocol to assist the dispatcher when communicating with the caller, the emergency dispatch protocol presenting a plurality of pre-scripted interrogatories for the dispatcher to ask the caller, and possible answers that the caller may provide, to collect information regarding the medical condition of the patient, wherein the emergency dispatch protocol is configured to generate an emergency medical dispatch response based on collected information to dispatch the emergency medical responders to the remote location;
    the dispatch center computer system initiating a diagnostic tool configured to aid the dispatcher in uniformly collecting from the caller information about the patient to aid in determining a vital sign of the patient, the diagnostic tool resident within a memory of the dispatch center computer system;
    the diagnostic tool providing instructions for the dispatcher to vocally relay to the caller over the telephonic call to assist the caller in providing information about the vital sign of the patient;
    the diagnostic tool receiving dispatcher-entered input indicative of the caller's observations regarding the vital sign of the patient, wherein the caller's observations are vocally relayed over the telephonic call to the dispatcher;
    relying only on the dispatcher-entered input indicative of the caller's observations as communicated vocally to the dispatcher, the diagnostic tool determining a vital sign of the patient; and
    the dispatch center computer system determining a priority for the emergency medical dispatch response based on the vital sign result determined by the diagnostic tool to thereby dispatch emergency medical responders according to the priority.

2. The computer implemented method of claim 1, wherein the dispatch center computer system determining the priority includes calculating a determinate value.

3. The computer implemented method of claim 1, further comprising:
    the diagnostic tool generating a recommendation based on the vital sign, and displaying the recommendation on a user interface of the dispatch center computer.

4. The computer implemented method of claim 1, wherein the vital sign is a breath rate.

5. The computer implemented method of claim 4, further comprising:
    the diagnostic tool providing instruction for the dispatcher to relay to the caller for measuring a breath rate.

6. The computer implemented method of claim 5, further comprising:
    the diagnostic tool displaying a measured breath rate on a user interface of the dispatch center computer.

7. The computer implemented method of claim 4, further comprising:
    the diagnostic tool providing instruction for the dispatcher to relay to the caller regarding a breath detection process for measuring a breath rate, the instruction including requesting that the caller communicate to the dispatcher each time a patient takes a breath during a period of time of the breath detection process;
    timing on the diagnostic tool a duration of the period of time of the breath detection process;
    receiving on the diagnostic tool dispatcher-entered input indicating that the caller communicated that the patient took a breath; and
    the diagnostic tool measuring the breath rate based on the duration of the time period of the breath detection process and the number of breaths taken during the time period.

8. The computer implemented method of claim 1, wherein the vital sign is a pulse rate.

9. The computer implemented method of claim 8, further comprising:
    the diagnostic tool providing instruction for the dispatcher to relay to the caller for taking a pulse.

10. The computer implemented method of claim 8, further comprising:
    the diagnostic tool displaying a measured pulse rate on a user interface of the dispatch center computer.

11. The computer implemented method of claim 8, further comprising:

the diagnostic tool providing instruction for the dispatcher to relay to the caller for taking a pulse, including counting a number of pulses during a period of time;

timing on the diagnostic tool a duration of the period of time;

receiving on the diagnostic tool dispatcher-entered input of a number of pulses counted by the caller during the time period; and the diagnostic tool calculating the pulse rate based on the duration of the period of time and the number of pulses counted.

12. The computer implemented method of claim 1, wherein the vital sign is a pregnancy contraction rate.

13. The computer implemented method of claim 12, further comprising:

the diagnostic tool providing instruction for the dispatcher to relay to the caller for taking a pregnancy contraction rate.

14. The computer implemented method of claim 12, further comprising:

the diagnostic tool displaying a measured pregnancy contraction rate on a user interface of the dispatch center computer.

15. The computer implemented method of claim 12, further comprising:

the diagnostic tool providing instruction for the dispatcher to relay to the caller regarding a contraction timing process for taking a pregnancy contraction rate, the instruction including that the caller communicate to the dispatcher each time the patient experiences a contraction during a period of time of the contraction timing process;

timing on the diagnostic tool a duration of the period of time of the contraction timing process;

receiving on the diagnostic tool dispatcher-entered input indicating that the caller communicated that the patient is experiencing a contraction; and the diagnostic tool calculating the pregnancy contraction rate based on the duration of the time period of the contraction timing process and the number of contractions experienced during the contraction timing process.

16. The computer implemented method of claim 1, further comprising the dispatch center computer system determining a vital sign result based on the determined vital sign.

17. The computer implemented method of claim 16, wherein the vital sign result is a categorization of the determined vital sign in one of a plurality of pre-determined categories.

18. The computer implemented method of claim 17, wherein the pre-determined categories include a normal category.

19. The computer implemented method of claim 17, wherein the vital sign result is displayed to provide indication to the dispatcher of the categorization of the vital sign.

20. A dispatch center computer system entirely disposed at a dispatch center to assist a dispatcher responding to a telephonic call from a caller regarding the medical condition of a patient to thereby enable determination of information about a vital sign of the patient without the assistance of medical equipment at the remote location of the caller and patient and to dispatch emergency medical responders to the remote location where the caller and patient are both present, the dispatch center computer system comprising:

a processor;

an input device in electrical communication with the processor; an output device in electrical communication with the processor; and a memory in electrical communication with the processor and comprising:

an emergency dispatch protocol module configured to present a plurality of prescripted interrogatories for the dispatcher to ask the caller and possible answers that the caller may provide to collect information regarding the medical condition of the patient, wherein the emergency dispatch protocol is configured to generate an emergency medical dispatch response based on the collected information to dispatch the emergency medical responders to the remote location; and a diagnostic tool operable by the processor and configured to:

provide instructions, displayed on the output device, for the dispatcher to vocally relay to the caller over the telephonic call to assist the caller in providing information about the vital sign of the patient;

receive dispatcher entered input, through the input device, indicative of the caller's observations regarding the vital sign of the patient, wherein the caller's observations are vocally relayed over the telephonic call to the dispatcher;

determine a vital sign of the patient based only on the dispatcher-entered input indicative of caller vocal communication; and determine a priority based on the vital sign for dispatching the emergency medical responders to the remote location of the caller and patient.

21. The dispatch center computer system of claim 20, wherein the diagnostic tool is further configured to generate a recommendation based on the vital sign and display the recommendation on the output device.

22. The dispatch center computer system of claim 20, wherein the vital sign is a breath rate.

23. The dispatch center computer system of claim 22, wherein the diagnostic tool is further configured to:

provide instruction for the dispatcher to relay to the caller for measuring a breath rate.

24. The dispatch center computer system of claim 22, wherein the diagnostic tool is further configured to display a measured breath rate on the output device.

25. The dispatch center computer system of claim 20, wherein the vital sign is a pulse rate.

26. The dispatch center computer system of claim 22, wherein the diagnostic tool is further configured to:

provide instruction for the dispatcher to relay to the caller regarding a breath detection process for measuring a breath rate, the instruction including requesting that the caller communicate to the dispatcher each time a patient takes a breath during a period of time of the breath detection process;

time a duration of the period of time of the breath detection process;

receive dispatcher-entered input indicating that the caller communicated that the patient took a breath; and calculate the breath rate based on the duration of the time period of the breath detection process and the number of breaths taken during the time period.

27. The dispatch center computer system of claim 25, wherein the diagnostic tool is further configured to:

provide instruction for the dispatcher to relay to the caller for taking a pulse.

28. The dispatch center computer system of claim 25, wherein the diagnostic tool is further configured to display a measured pulse rate on the output device.

29. The dispatch center computer system of claim 25, wherein the diagnostic tool is further configured to:
provide instruction for the dispatcher to relay to the caller for taking a pulse, including counting a number of pulses during a period of time;
time a duration of the period of time;
receive on the diagnostic tool dispatcher-entered input of a number of pulses counted by the caller during the time period; and
calculate the pulse rate based on the duration of the period of time and the number of pulses counted.

30. The dispatch center computer system of claim 20, wherein the vital sign is a pregnancy contraction rate.

31. The dispatch center computer system of claim 30, wherein the diagnostic tool is further configured to provide instruction for the dispatcher to relay to the caller for taking a pregnancy contraction rate.

32. The dispatch center computer system of claim 30, wherein the diagnostic tool is further configured to display a measured pregnancy contraction rate on the output device.

33. The dispatch center computer system of claim 30, wherein the diagnostic tool is further configured to provide instruction for the dispatcher to relay to the caller for taking a pregnancy contraction rate, the instruction including that the caller communicate to the dispatcher each time the patient experiences a contraction during a period of time of the contraction timing process;
time on the diagnostic tool a duration of the period of time of the contraction timing process;
receive dispatcher-entered input indicating that the caller communicated that the patient is experiencing a contraction; and
calculate the pregnancy contraction rate based on the duration of the time period of the contraction timing process and the number of contractions experienced during the contraction timing process.

34. The dispatch center computer system of claim 20, wherein the diagnostic tool is further configured to determine a vital sign result based on the determined vital sign.

35. The dispatch center computer system of claim 34, wherein the vital sign result categorizes the determined vital sign in one of a plurality of pre-determined categories.

36. The computer implemented method of claim 35, wherein the vital sign result is displayed to provide indication to the dispatcher of the categorization of the vital sign.

37. A non-transitory computer readable storage medium comprising computer readable instruction code for a method performed entirely by a dispatch center computer system at a dispatch center to assist a dispatcher responding to a telephonic call from a caller regarding the medical condition of a patient to thereby enable determination of information about a vital sign of the patient without the assistance of medical equipment at a remote location of the caller and patient, the dispatcher to dispatch emergency medical responders to the remote location where the caller and patient are both present, the method comprising:
providing an emergency dispatch protocol to assist the dispatcher when communicating with the caller, the emergency dispatch protocol including a plurality of pre-scripted interrogatories for the dispatcher to ask the caller and possible answers that the caller may provide to collect information regarding the medical condition of the patient, wherein the dispatch protocol is configured to generate an emergency medical dispatch response based on the collected information to dispatch the emergency medical responders to the remote location;
initiating a diagnostic tool on the dispatch center computer system, the diagnostic tool configured to aid the dispatcher in uniformly collecting from the caller information about the patient to aid in determining a vital sign of the patient, the diagnostic tool resident within a memory of the dispatch center computer system;
the diagnostic tool providing instructions for the dispatcher to vocally relay to the caller over the telephonic call to assist the caller in providing information about the vital sign of the patient;
the diagnostic tool receiving dispatcher entered input indicative of the caller's observations regarding the vital sign of the patient, wherein the caller's observations are vocally relayed over the telephonic call to the dispatcher;
relying only on the dispatcher entered input indicative of the caller's observations as communicated vocally by the caller to the dispatcher, the diagnostic tool determining a vital sign of the patient; and
determining a priority for the emergency medical dispatch response based on the vital sign determined by the diagnostic tool to thereby dispatch emergency medical responders according to the priority.

38. The computer readable storage medium of claim 37, wherein determining the priority includes calculating a determinant value.

39. The computer readable storage medium of claim 37, wherein the method further comprises:
the diagnostic tool generating a recommendation, based on the vital sign, and displaying the recommendation on a user interface of the dispatch center computer.

40. The computer readable storage medium of claim 37, wherein the vital sign is a breath rate.

41. The computer readable storage medium of claim 40, wherein the method further comprises:
the diagnostic tool providing instruction for the dispatcher to relay to the caller for measuring a breath rate.

42. The computer readable storage medium of claim 40, wherein the method further comprises:
the diagnostic tool displaying a measured breath rate on a user interface of the dispatch center computer.

43. The computer readable storage medium of claim 40, wherein the method further comprises:
the diagnostic tool providing instruction for the dispatcher to relay to the caller regarding a breath detection process for measuring a breath rate, the instruction including requesting that the caller communicate to the dispatcher each time a patient takes a breath during a period of time of the breath detection process;
timing on the diagnostic tool a duration of the period of time of the breath detection process;
receiving on the diagnostic tool dispatcher-entered input indicating that the caller communicated that the patient took a breath; and
the diagnostic tool calculating the breath rate based on the duration of the time period of the breath detection process and the number of breaths taken during the time period.

44. The computer readable storage medium of claim 37, wherein the vital sign is a pulse rate.

45. The computer readable storage medium of claim 44, wherein the method further comprises:
the diagnostic tool providing instruction for the dispatcher to relay to the caller for taking a pulse.

46. The computer readable storage medium of claim 44, wherein the method further comprises:
the diagnostic tool displaying a measured pulse rate on a user interface of the dispatch center computer.

47. The computer readable storage medium of claim 44, wherein the method further comprises:
- the diagnostic tool providing instruction for the dispatcher to relay to the caller for taking a pulse, including counting a number of pulses during a period of time;
- timing on the diagnostic tool a duration of the period of time;
- receiving on the diagnostic tool dispatcher-entered input of a number of pulses counted by the caller during the time period; and
- the diagnostic tool calculating the pulse rate based on the duration of the period of time and the number of pulses counted.

48. The computer readable storage medium of claim 37, wherein the vital sign is a pregnancy contraction rate.

49. The computer readable storage medium of claim 48, wherein the method further comprises:
- the diagnostic tool providing instruction for the dispatcher to relay to the caller for taking a pregnancy contraction rate.

50. The computer readable storage medium of claim 48, wherein the method further comprises:
- the diagnostic tool displaying a measured pregnancy contraction rate on a user interface of the dispatch center computer.

51. The computer readable storage medium of claim 48, wherein the method further comprises:
- the diagnostic tool providing instruction for the dispatcher to relay to the caller regarding a contraction timing process for taking a pregnancy contraction rate, the instruction including that the caller communicate to the dispatcher each time the patient experiences a contraction during a period of time of the contraction timing process;
- timing on the diagnostic tool a duration of the period of time of the contraction timing process;
- receiving on the diagnostic tool dispatcher-entered input indicating that the caller communicated that the patient is experiencing a contraction; and
- the diagnostic tool calculating the pregnancy contraction rate based on the duration of the time period of the contraction timing process and the number of contractions experienced during the contraction timing process.

52. The computer readable storage medium of claim 37, wherein the method further comprises determining a vital sign result based on the determined vital sign.

53. The computer readable storage medium of claim 52, wherein the vital sign result categorizes the determined vital sign in one of a plurality of pre-determined categories.

54. The computer readable storage medium of claim 53, wherein the vital sign result is displayed to provide indication to the dispatcher of the categorization of the vital sign.

55. A computer implemented method performed entirely by a dispatch center computer system at a dispatch center to assist a dispatcher responding to a telephonic call from a caller regarding the medical condition of the caller to thereby enable determination of information about a vital sign of the caller without the assistance of medical equipment at a remote location of the caller, the dispatcher to dispatch emergency medical responders to the remote location where the caller is present, the method comprising:
- providing on the dispatch center computer sytem an emergency dispatch protocol to assist the dispatcher when communicating with the caller, the emergency dispatch protocol presenting a plurality of pre-scripted interrogatories for the dispatcher to ask the caller and possible answers that the caller may provide to collect information regarding the medical condition of the caller, wherein the emergency dispatch protocol is configured to generate an emergency medical dispatch response based on the collected information to dispatch the emergency medical responders to the remote location;
- initiating a diagnostic tool on the dispatch center computer system, the diagnostic tool configured to aid the dispatcher in uniformly collecting information from the caller to aid in determining a vital sign of the caller, the diagnostic tool resident within a memory of the dispatch center computer system;
- the diagnostic tool providing instructions for the dispatcher to vocally relay to the caller over the telephonic call to assist the caller in providing information about the vital sign of the caller;
- the diagnostic tool receiving dispatcher entered input indicative of the caller's observations regarding the caller's vital sign, wherein the caller's observations are vocally relayed over the telephonic call to the dispatcher;
- relying only on the dispatcher entered input indicative of caller vocal communication, the diagnostic tool determining a vital sign of the caller; and
- the dispatch center computer system determining a priority for the emergency medical dispatch response based on the vital sign determined by the diagnostic tool to thereby dispatch emergency medical responders according to the priority.

56. The computer-implemented method of claim 55, wherein the method further comprises determining a vital sign result based on the determined vital sign.

57. The computer-implemented method of claim 56, wherein the vital sign result categorizes the determined vital sign in one of a plurality of pre-determined categories.

58. The computer-implemented method of claim 57, wherein the vital sign result is displayed to provide indication to the dispatcher of the categorization of the vital sign.

59. A non-transitory computer readable storage medium comprising computer readable instruction code for a method performed entirely by a dispatch center computer system at a dispatch center to assist a dispatcher responding to a telephonic call from a caller regarding the medical condition of a caller to thereby enable determination of information about a vital sign of the caller without the assistance of medical equipment at a remote location of the caller, the dispatcher to dispatch emergency medical responders to the remote location where the caller is present, the method comprising:
- providing an emergency dispatch protocol to assist the dispatcher when communicating with the caller, the emergency dispatch protocol including a plurality of pre-scripted interrogatories for the dispatcher to ask the caller and possible answers that the caller may provide to collect information regarding the medical condition of the caller, wherein the dispatch protocol is configured to generate an emergency medical dispatch response based on the collected information to dispatch the emergency medical responders to the remote location;
- initiating a diagnostic tool on the dispatch center computer system, the diagnostic tool configured to aid the dispatcher in uniformly collecting from the caller information about the patient to aid in determining a vital sign of the patient, the diagnostic tool resident within a memory of the dispatch center computer system;
- the diagnostic tool providing instructions for the dispatcher to vocally relay to the caller over the telephonic call to assist the caller in providing information about the vital sign of the caller;

the diagnostic tool receiving dispatcher entered input indicative of the caller's observations regarding the vital sign of the caller, wherein the caller's observations are vocally relayed over the telephonic call to the dispatcher;

relying only on the dispatcher-entered input indicative of caller vocal communication, the diagnostic tool determining a vital sign of the caller; and determining a priority for the emergency medical dispatch response based on the vital sign determined by the diagnostic tool to thereby dispatch emergency medical responders according to the priority.

60. The non-transitory computer readable storage medium of claim 59, wherein the method further comprises determining a vital sign result based on the determined vital sign.

61. The non-transitory computer readable storage medium of claim 60, wherein the vital sign result categorizes the determined vital sign in one of a plurality of pre-determined categories.

62. The non-transitory computer readable storage medium of claim 61, wherein the vital sign result is displayed to provide indication to the dispatcher of the categorization of the vital sign.

* * * * *

UNITED STATES PATENT AND TRADEMARK OFFICE
CERTIFICATE OF CORRECTION

PATENT NO.         : 8,066,638 B2
APPLICATION NO.    : 12/396201
DATED              : November 29, 2011
INVENTOR(S)        : Clawson It is certified that error appears in the above-identified patent and that said Letters Patent is hereby corrected as shown below:

Column 4, Line 67 reads, "...intervals are shown are shown in..." which should read, "...intervals are shown in..."

Column 6, Line 15 reads, "...based on the Dispatcher's input..." which should read, "...based on the dispatcher's input..."

Column 9, Line 26 reads, "...assist emergency responder prior to arrival." which should read, "...assist emergency responders prior to arrival."

Column 12, Line 4 reads, "...present a plurality of prescripted interrogatories..." which should read, "...present a plurality of pre-scripted interrogatories..."

Column 12, Line 20 reads, "...receive a dispatcher entered input..." which should read, "...receive a dispatcher-entered input..."

Column 14, Line 11 reads, "...receiving dispatcher entered input..." which should read, "...receiving dispatcher-entered input..."

Column 14, Line 16 reads, "...the dispatcher entered input..." which should read, "...the dispatcher-entered input..."

Column 15, Line 62 reads, "on the dispatch center computer sytem" should read, "...on the dispatch computer system..."

Column 16, Line 16 reads, "...receiving dispatcher entered input..." which should read, "...receiving dispatcher-entered input..."

Column 16, Line 21 reads, "...the dispatcher entered input..." which should read, "...the dispatcher-entered input..."

Signed and Sealed this
Fourteenth Day of February, 2012

David J. Kappos
*Director of the United States Patent and Trademark Office*

Column 17, Line 1 reads, "...receiving dispatcher entered input..." which should read, "...receiving dispatcher-entered input..."